(12) United States Patent
Esue et al.

(10) Patent No.: US 9,254,321 B2
(45) Date of Patent: Feb. 9, 2016

(54) COMPOSITIONS AND METHODS FOR STABILIZING PROTEIN-CONTAINING FORMULATIONS

(71) Applicant: Genentech, Inc., South San Francisco, CA (US)

(72) Inventors: Osigwe Esue, San Mateo, CA (US); Vikas K. Sharma, Milbrae, CA (US)

(73) Assignee: Genentech, Inc., South San Francisco, CA (US)

( * ) Notice: Subject to any disclaimer, the term of this patent is extended or adjusted under 35 U.S.C. 154(b) by 365 days.

(21) Appl. No.: 13/722,559

(22) Filed: Dec. 20, 2012

(65) Prior Publication Data

US 2013/0224213 A1    Aug. 29, 2013

Related U.S. Application Data

(63) Continuation of application No. PCT/US2011/041598, filed on Jun. 23, 2011.

(60) Provisional application No. 61/358,105, filed on Jun. 24, 2010.

(51) Int. Cl.

| A61K 39/395 | (2006.01) |
|---|---|
| C07K 16/00 | (2006.01) |
| C07K 16/28 | (2006.01) |
| C07K 16/30 | (2006.01) |
| A61K 9/00 | (2006.01) |
| A61K 47/10 | (2006.01) |
| A61K 9/19 | (2006.01) |

(52) U.S. Cl.
CPC ......... *A61K 39/39591* (2013.01); *A61K 9/0019* (2013.01); *A61K 9/19* (2013.01); *A61K 47/10* (2013.01); *C07K 16/00* (2013.01); *C07K 16/2803* (2013.01); *C07K 16/2845* (2013.01); *C07K 16/3092* (2013.01)

(58) Field of Classification Search
None
See application file for complete search history.

(56) References Cited

U.S. PATENT DOCUMENTS

| 6,171,586 B1 * | 1/2001 | Lam et al. ................. 424/130.1 |
| 2007/0111938 A1 | 5/2007 | Pert et al. |

FOREIGN PATENT DOCUMENTS

| EP | 0 109 942 | 5/1984 |
| EP | 0 231 039 | 8/1987 |
| JP | 2004-526674 A | 9/2004 |
| WO | 97/04801 | 2/1997 |
| WO | 02/43750 A2 | 6/2002 |
| WO | 2007/149096 | 12/2007 |
| WO | 2008/012062 | 1/2008 |
| WO | 2010/151703 | 12/2010 |

OTHER PUBLICATIONS

Choplin, L. et al., "Phase behavior and rheological properties of enzymatically synthesized trehalose decanoate aqueous solutions" Journal of Colloid Interface Science 294:187-193 (Feb. 1, 2006).
International Search Report of PCT/US2011/041598; Publication No. WO 2011/163458, pp. 1-5 (Dec. 29, 2011).
Grune et al., "Degradation of oxidized proteins in mammalian cells," FASEB J., 11: 526-534 (1997).

* cited by examiner

*Primary Examiner* — Yunsoo Kim
(74) *Attorney, Agent, or Firm* — McNeill Baur PLLC

(57) ABSTRACT

The present invention relates to use of certain alkylglycoside compositions for the prevention of aggregation and oxidation of antibodies and other proteins in therapeutically useful formulations thereof.

18 Claims, 16 Drawing Sheets

COMPOSITIONS AND METHODS FOR STABILIZING PROTEIN-CONTAINING FORMULATIONS

CROSS-REFERENCE TO RELATED APPLICATIONS

This application claims the benefit of International Application No. PCT/US2011/041598, filed Jun. 23, 2011, which claims priority to U.S. Provisional Application No. 61/358,105, filed Jun. 24, 2010, the contents of which are hereby incorporated by reference in their entirety for all purposes.

FIELD OF THE INVENTION

The present invention relates to use of certain alkylglycoside compositions for the prevention of aggregation and oxidation of antibodies and other proteins in therapeutically useful formulations thereof.

BACKGROUND OF THE INVENTION

When a stabilizer for a protein formulation is needed to protect a protein from denaturation upon shaking, agitation, shearing and freeze thaw, or in quiescent state at interface, a nonionic detergent (i.e., a surfactant) is often used (see, e.g., U.S. Pat. No. 5,183,746). This is exemplified by the use of polysorbates in many protein-containing products. For example, polysorbates 20 and 80 (Tween® 20 and Tween® 80) are used in the formulation of biotherapeutic products for both preventing surface adsorption and as stabilizers against protein aggregation (Kerwin, J. Pharm. Sci. 97(8):2924-2936 (2008)). The polysorbates are amphipathic, nonionic surfactants composed of fatty acid esters of polyoxyethylene (POE) sorbitan, being polyoxyethylene sorbitan monolaurate for polysorbate 20 and polyoxyethylene sorbitan monooleate for polysorbate 80.

Unfortunately, however, polysorbates can undergo degradation via either oxidation or hydrolysis. When a polysorbate molecule degrades, it generates various degradation byproducts including, for example, fatty acids, POE sorbitan, PEG, PEG esters and alkyl acids. Certain of these byproducts of polysorbate degradation, including the free fatty acids, can cause increased turbidity of and protein aggregation in protein-containing formulations. Therefore, while polysorbates are commonly used as protein stabilizers, the fatty acids and other degradation byproducts released from polysorbate degradation over time can adversely impact the protective effect that polysorbates exhibit in protein-containing formulations.

Proteins undergo varying degrees of degradation during purification and storage, wherein oxidation (including, light-induced oxidation) is one of the major degradation pathways that has a destructive effect on protein stability and potency. Oxidative reactions cause destruction of amino acid residues, peptide bond hydrolysis, and hence protein instability due to alteration of the protein's tertiary structure and protein aggregation (Davies, J. Biol. Chem. 262: 9895-901 (1987)). Oxidation of protein pharmaceuticals have been reviewed by Nguyen (Chapter 4 in Formulation and Delivery of Protein and Peptides (1994)), Hovorka, (J. Pharm Sci. 90:25369 (2001)) and Li (Biotech Bioengineering 48:490-500 (1995)).

Given the above, it is evident that there is a need for the identification of compositions useful for enhancing the stability and preventing the aggregation and/or oxidation of proteins in protein-containing formulations.

SUMMARY OF THE INVENTION

The present invention is based upon the novel finding that certain alkylglycoside compositions are useful for stabilizing and/or reducing aggregation or immunogenicity of antibodies or other proteins in therapeutically useful formulations. Moreover, the present invention is further based upon the novel finding that certain alkylglycoside compositions are useful for preventing the oxidation of amino acid residues, particularly tryptophan residues, on antibodies or other proteins in therapeutically useful formulations. More specifically, one aspect of the present invention is directed to methods of using alkylglycosides having a critical micelle concentration (CMC) value of at least 1.0 mM as protein stabilizing, or aggregation-reducing, agents. In certain embodiments of the present invention, the alkylglycoside composition is used in the antibody- or other protein-containing formulation at a concentration that is below its respective CMC value.

Accordingly, in one aspect, the present invention relates to a composition of matter comprising a protein and an alkylglycoside having a CMC value of about 1.0 mM or greater in water at 25° C. In certain embodiments, the protein present in the composition of matter is an antibody, which may optionally be a monoclonal antibody. In yet other embodiments, the alkylglycoside is selected from the group consisting of n-hexyl-β-D-glucopyranoside, n-heptyl-β-D-glucopyranoside, n-octyl-β-D-glucopyranoside, n-nonyl-β-D-glucopyranoside, n-decyl-β-D-glucopyranoside, 3-cyclohexyl-1-propyl-β-D-glucoside, 3-cyclohexyl-1-butyl-β-D-glucoside, n-hexyl-β-D-maltopyranoside, n-octyl-β-D-maltopyranoside, n-nonyl-β-D-maltopyranoside, n-decyl-β-D-maltopyranoside, cyclohexyl-methyl-β-D-maltoside, 2-cyclohexyl-ethyl-β-D-maltoside, 3-cyclohexyl-propyl-β-D-maltoside, 4-cyclohexyl-butyl-β-D-maltoside, and 5-cyclohexyl-pentyl-β-D-maltoside. In yet other embodiments, the composition of matter comprises an agitation-induced aggregation inhibiting amount or an oxidation preventing amount of the alkylglycoside. In yet another embodiment, the alkylglycoside is present in the composition of matter at a concentration that is lower than the CMC value of the alkylglycoside in water at 25° C. the composition of matter may be aqueous, may be stable at a temperature of about 2-8° C. for at least one year, and/or may be stable at a temperature of about 30° C. for at least one month. Optionally, the composition of matter is not lyophilized and is not subjected to prior lyophilization or may be a reconstituted lyophilized formulation.

In another aspect, the present invention is directed to an article of manufacture comprising a container holding the above described composition of matter.

Yet another aspect of the present invention is directed to a making a pharmaceutical formulation comprising preparing the above described composition of matter and evaluating the physical stability, chemical stability, or biological activity of the protein in the composition of matter.

Yet another aspect of the present invention is directed to a method of inhibiting agitation-induced aggregation of a protein present in an first aqueous solution, wherein the method comprises the step of adding to the first aqueous solution an agitation-induced aggregation inhibiting amount of an alkylglycoside having a CMC value of about 1.0 mM or greater in water at 25° C., thereby providing a second aqueous solution.

Yet another aspect of the present invention is directed to a method of preventing the oxidation of a protein present in an first aqueous solution, wherein the method comprises the step of adding to the first aqueous solution an oxidation inhibiting amount of an alkylglycoside having a CMC value of about 1.0 mM or greater in water at 25° C., thereby providing a second aqueous solution.

DETAILED DESCRIPTION OF THE PREFERRED EMBODIMENT

Figure 1:
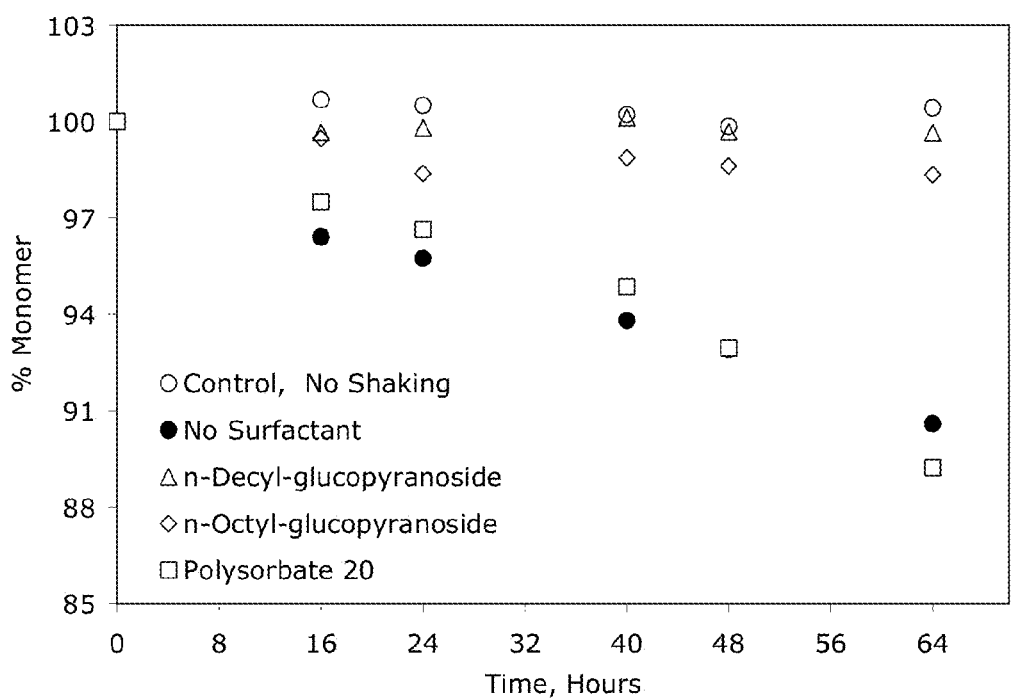
FIG. 1 shows the effect of certain surfactants on agitation-induced aggregation of an anti-MUC16 monoclonal antibody in aqueous solution.

The present invention may be understood more readily by reference to the following detailed description of specific embodiments and the Examples included therein.

Unless defined otherwise, all technical and scientific terms used herein have the same meaning as commonly understood by one of ordinary skill in the art to which this invention belongs. Although any methods and materials similar or equivalent to those described herein can be used in the practice or testing of the invention, the preferred methods and materials are now described. All publications mentioned herein are incorporated herein by reference in their entirety.

Herein, numerical ranges or amounts prefaced by the term "about" expressly include the exact range or exact numerical amount.

Aggregation of antibodies and other proteins is caused mainly by hydrophobic interactions that eventually lead to denaturation. When the hydrophobic region of a partially or fully unfolded protein is exposed to water, this creates a thermodynamically unfavorable situation due to the fact that the normally buried hydrophobic interior is now exposed to a hydrophilic aqueous environment. Consequently, the decrease in entropy from structuring water molecules around the hydrophobic region forces the denatured protein to aggregate, mainly through the exposed hydrophobic regions. Thus, solubility of the protein may also be compromised. In some cases, self-association of protein subunits, either native or misfolded, may occur under certain conditions and this may lead to precipitation and loss in activity.

Factors that affect protein aggregation in solution generally include protein concentration, pH, temperature, other excipients, and mechanical stress. Some factors (e.g., temperature) can be more easily controlled during purification, compounding, manufacturing, storage and use than others (e.g., mechanical stress). Formulation studies will dictate appropriate choice(s) of pH and excipients that will not induce aggregation and/or, in fact, will aid in the prevention of aggregation. Protein concentration is dictated by the required therapeutic dose and, depending on what this concentration is, will determine whether the potential for higher associated states (dimers, tetramers, etc.) exists, which can then lead to aggregation in solution. Careful studies must be done during formulation development to determine what factors influence protein aggregation and then how these factors can be eliminated or controlled.

The desire to identify stable solution preparations of an antibody or other protein for use in parenteral or other administration can lead to the development of test methodology for assessing the impact of various additives on physical stability. Based on the known factors influencing protein aggregation and the requirements of such applications, physical stability may be evaluated using mechanical procedures involving agitation or rotation of protein solutions. The methodology for physical stress testing to identify the capability of various additives to prevent aggregation might involve exposure to shaking or stirring in the horizontal plane or rotation x cm from the axis of a wheel rotating at n rev/min in the vertical plane. Turbidity resulting from aggregation is usually determined as a function of time by visual inspection or light scattering analysis. Alternatively, reductions in the soluble protein content due to precipitation can be quantitated by HPLC assay as a function of time.

The present invention is based upon the novel finding that that certain alkylglycoside compositions are useful for stabilizing or reducing aggregation and immunogenicity of antibodies or other proteins in therapeutically useful formulations. Moreover, the present invention is further based upon the novel finding that that certain alkylglycoside compositions are useful for preventing or reducing the oxidation of antibodies or other proteins in therapeutically useful formulations.

"Surfactants" are surface active agents that can exert their effect at surfaces of solid-solid, solid-liquid, liquid-liquid, and liquid-air because of their chemical composition, containing both hydrophilic and hydrophobic groups. These materials reduce the concentration of proteins in dilute solutions at the air-water and/or water-solid interfaces where proteins can be adsorbed and potentially aggregated. Surfactants can bind to hydrophobic interfaces in protein formulations.

Proteins on the surface of water will aggregate, particularly when agitated, because of unfolding and subsequent aggregation of the protein monolayer.

"Surfactants" can denature proteins, but can also stabilize them against surface denaturation. Generally, ionic surfactants can denature proteins. However, nonionic surfactants usually do not denature proteins even at relatively high concentrations (1% w/v). Most parentally acceptable nonionic surfactants come from either the polysorbate or polyether groups. Polysorbate 20 and 80 are contemporary surfactant stabilizers in marketed protein formulations. However, other surfactants used in protein formulations include Pluronic F-68 and members of the "Brij" class. None of these are alkylglycosides of the present invention.

Physical events can result in exposure to chemical events. The chemical instability of proteins can involve the cleavage or formation of covalent bonds with the protein primary structure. Several oxidation reactions in proteins have been reported. In the alkaline or neutral medium the residues of the amino acids cysteine, histidine, methionine, tryptophan and tyrosine are especially prone to oxidation. In acidic conditions, however, methionine is sensitive. Often the oxidation reactions cause a great loss in biological activity and even immunogenicity. It is well known in the art that oxidation of amino acid residues in proteins, especially tryptophan residues, may be induced by exposure to light.

Peroxides are known contaminants of non-ionic surfactants. Peroxides in polysorbates can result in oxidative degradation of proteins. Formulators tend to screen sources of polysorbates and other polymeric additives in protein formulations for peroxide contamination and establish peroxide specifications for using the additive. Alternatively, incorporation of an antioxidant is used to help to overcome the potential for non-ionic surfactants to serve as oxidative catalysts for oxygen-sensitive proteins.

"Surfactants" are molecules with well defined polar and non-polar regions that allow them to aggregate in solution to form micelles. Depending on the nature of the polar area, surfactants can be non-ionic, anionic, cationic, and Zwitterionic. Non-ionic surfactants can be sugar-based. Sugar-based surfactants can be alkylglycosides.

As used herein, "alkylglycoside" refers to any sugar joined by a linkage to any hydrophobic alkyl, as is known in the art. The linkage between the hydrophobic alkyl chain and the hydrophilic saccharide can include, among other possibilities, a glycosidic, ester, thioglycosidic, thioester, ether, amide or ureide bond or linkage. Examples of which are described herein. The terms alkylglycoside and alkylsaccharide may be used interchangeably herein.

The general structure of the alkylglycosides of the present invention is $R_1$—O—$(CH_2)_x$—R, where R may be, for example, $CH_3$, cyclohexyl ($C_6H_{11}$), or another alkyl chain, including the isomers thereof, and $R_1$ is a sugar, typically glucose or maltose. Exemplary alkylglycosides include those in which $R_1$ is glucose, R is $CH_3$, and x is 5 (n-hexyl-β-D-glucopyranoside), x is 6 (n-heptyl-β-D-glucopyranoside), x is 7 (n-octyl-β-D-glucopyranoside), x is 8 (n-nonyl-β-D-glucopyranoside), x is 9 (n-decyl-β-D-glucopyranoside), and x is 11 (n-dodecyl-β-D-glucopyranoside). Sometimes glucopyranosides are called glucosides.

Exemplary alkylglycosides additionally include those in which $R_1$ is maltose, R is $CH_3$, and x is 5 (n-hexyl-β-D-maltopyranoside), x is 7 (n-octyl-β-D-maltopyranoside), x is 8 (n-nonyl-β-D-maltopyranoside), x is 9 (n-decyl-β-D-maltopyranoside), x is 10 (n-undecyl-(3-D-maltopyranoside), x is 11 (n-dodecyl-β-D-maltopyranoside), x is 12 (n-tridecyl-β-D-maltopyranoside), x is 13 (n-tetradecyl-β-D-maltopyranoside), and x is 15 (n-hexadecyl-β-D-maltopyranoside). Sometimes maltopyranosides are called maltosides.

Exemplary alkylglycosides further include those in which $R_1$ is glucose, x is 3, and R is cyclohexyl(3-cyclohexyl-1-propyl-β-D-glucoside); and in which $R_1$ is maltose, x is 4, and R is cyclohexyl(4-cyclohexyl-1-butyl-β-D-maltoside).

In one specific aspect of the present invention, alkylglycosides employed in the present invention are those that exhibit a critical micelle concentration (CMC) value of about 1.0 mM or greater in water at between 20-25° C., preferably at 25° C. Exemplary alkylglycosides having such CMC values are shown in Table I below, wherein others are well known in the art.

TABLE I

| Alkylglycoside | CMC Value (mM) | CMC Value (w/v) |
| --- | --- | --- |
| n-hexyl-β-D-glucopyranoside | 250 mM | 6.6% w/v |
| n-heptyl-β-D-glucopyranoside | 70 mM | 1.9% w/v |
| n-octyl-β-D-glucopyranoside | 18 mM | 0.53% w/v |
| n-nonyl-β-D-glucopyranoside | 6.5 mM | 0.2% w/v |
| n-decyl-β-D-glucopyranoside | 2.2 mM | 0.07% w/v |
| 3-cyclohexyl-1-propyl-β-D-glucoside | 28 mM | 0.86% w/v |
| 3-cyclohexyl-1-butyl-β-D-glucoside | 1.8 mM | 0.058% w/v |
| n-hexyl-β-D-maltopyranoside | 210 mM | 8.9% w/v |
| n-octyl-β-D-maltopyranoside | 19.5 mM | 0.89% w/v |
| n-nonyl-β-D-maltopyranoside | 6 mM | 0.28% w/v |
| n-decyl-β-D-maltopyranoside | 1.8 mM | 0.087% w/v |
| cyclohexyl-methyl-β-D-maltoside | 340 mM | 15% w/v |
| 2-cyclohexyl-ethyl-β-D-maltoside | 120 mM | 5.4% w/v |
| 3-cyclohexyl-propyl-β-D-maltoside | 34.5 mM | 1.6% w/v |
| 4-cyclohexyl-butyl-β-D-maltoside | 7.6 mM | 0.37% w/v |
| 5-cyclohexyl-pentyl-β-D-maltoside | 2.4 mM | 0.12% w/v |
| n-dodecyl-β-D-maltopyranoside | 0.17 mM | 0.0087 w/v |
| n-dodecyl-β-D-glucopyranoside | 0.19 mM | 0.0066 w/v |

A particular alkylglycoside may be employed singly as an antibody or other protein stabilizing (or aggregation- or oxidation-reducing) agent, or may be employed in combination with other alkylglycosides. Alkylglycosides find use as antibody or other protein stabilizing (or anti-aggregation or anti-oxidation) agents across a wide range of concentrations in aqueous solution. In particular embodiments of the present invention, the alkylglycoside (if employed as a single agent) or alkylglycosides (if employed in combination) may be present in the aqueous antibody- or other protein-containing formulation at a concentration of from about 0.001 mM to about 500 mM, more preferably from about 0.005 mM to about 400 mM, more preferably from about 0.01 mM to about 300 mM, more preferably from about 0.02 mM to about 250 mM, more preferably from about 0.03 mM to about 200 mM, more preferably from about 0.05 mM to about 100 mM, more preferably from about 0.1 mM to about 100 mM, more preferably from about 0.1 mM to about 50 mM.

In a particularly preferred embodiment of the present invention, a particular alkylglycoside may be employed as an antibody or other protein stabilizing (or aggregation- or oxidation-reducing) agent at a concentration that is lower than its respective CMC value.

In regard to the above, it is understood in the art that the chemical synthesis of compounds such as the alkylglycosides described herein results in a somewhat heterogeneous mixture of compounds, rather than a completely homogeneous preparation. As such, when it is herein described that a particular alkylglycoside is employed, it is to be understood that that definition refers to the majority components of the heterogeneous mixture that result from the chemical synthesis thereof.

By "polypeptide" or "protein" is meant a sequence of amino acids for which the chain length is sufficient to produce the higher levels of tertiary and/or quaternary structure. Thus, proteins are distinguished from "peptides" which are also amino acid-based molecules that do not have such structure. Typically, a protein for use herein will have a molecular weight of at least about 5-20 kD, alternatively at least about 15-20 kD, preferably at least about 20 kD. "Peptide" is meant a sequence of amino acids that generally does not exhibit a higher level of tertiary and/or quaternary structure. Peptides generally have a molecular weight of less than about 5 kD.

Examples of polypeptides encompassed within the definition herein include mammalian proteins, such as, e.g., renin; a growth hormone, including human growth hormone and bovine growth hormone; growth hormone releasing factor; parathyroid hormone; thyroid stimulating hormone; lipoproteins; alpha-1-antitrypsin; insulin A-chain; insulin B-chain; proinsulin; follicle stimulating hormone; calcitonin; luteinizing hormone; glucagon; clotting factors such as factor VIIIC, factor IX, tissue factor, and von Willebrands factor; anti-clotting factors such as Protein C; atrial natriuretic factor; lung surfactant; a plasminogen activator, such as urokinase or human urine or tissue-type plasminogen activator (t-PA); bombesin; thrombin; hemopoietic growth factor; tumor necrosis factor-alpha and -beta; enkephalinase; RANTES (regulated on activation normally T-cell expressed and secreted); human macrophage inflammatory protein (MIP-1-alpha); a serum albumin such as human serum albumin; Muellerian-inhibiting substance; relaxin A-chain; relaxin B-chain; prorelaxin; mouse gonadotropin-associated peptide; a microbial protein, such as beta-lactamase; DNase; IgE; a cytotoxic T-lymphocyte associated antigen (CTLA), such as CTLA-4; inhibin; activin; vascular endothelial growth factor (VEGF); receptors for hormones or growth factors; protein A or D; rheumatoid factors; a neurotrophic factor such as bone-derived neurotrophic factor (BDNF), neurotrophin-3, -4, -5, or -6 (NT-3, NT-4, NT-5, or NT-6), or a nerve growth factor such as NGF-β; platelet-derived growth factor (PDGF); fibroblast growth factor such as aFGF and bFGF; epidermal growth factor (EGF); transforming growth factor (TGF) such as TGF-alpha and TGF-beta, including TGF-β1, TGF-β2, TGF-β3, TGF-β4, or TGF-β5; insulin-like growth factor-I and -II (IGF-I and IGF-II); des(1-3)-IGF-I (brain IGF-I), insulin-like growth factor binding proteins (IGFBPs); CD proteins such as CD3, CD4, CD8, CD19 and CD20; erythropoietin; osteoinductive factors; immunotoxins; a bone morphogenetic protein (BMP); an interferon such as interferon-alpha, -beta, and -gamma; colony stimulating factors (CSFs), e.g., M-CSF, GM-CSF, and G-CSF; interleukins (ILs), e.g., IL-1 to IL-10; superoxide dismutase; T-cell receptors; surface membrane proteins; decay accelerating factor; viral antigen such as, for example, a portion of the AIDS envelope; transport proteins; homing receptors; addressins; regulatory proteins; integrins such as CD11a, CD11b, CD11c, CD18, an ICAM, VLA-4 and VCAM; a tumor associated antigen such as CA125 (ovarian cancer antigen) or HER2, HER3 or HER4 receptor; immunoadhesins; and fragments and/or variants of any of the above-listed proteins as well as antibodies, including antibody fragments, binding to any of the above-listed proteins.

The protein which is formulated is preferably essentially pure and desirably essentially homogeneous (i.e., free from contaminating proteins). "Essentially pure" protein means a composition comprising at least about 90% by weight of the protein, based on total weight of the composition, preferably at least about 95% by weight. "Essentially homogeneous" protein means a composition comprising at least about 99% by weight of protein, based on total weight of the composition.

In certain embodiments, the protein is an antibody. The antibody herein is directed against an "antigen" of interest. Preferably, the antigen is a biologically important protein and administration of the antibody to a mammal suffering from a disease or disorder can result in a therapeutic benefit in that mammal. However, antibodies directed against non-protein antigens (such as tumor-associated glycolipid antigens; see U.S. Pat. No. 5,091,178) are also contemplated. Where the antigen is a protein, it may be a transmembrane molecule (e.g., receptor) or ligand such as a growth factor. Exemplary antigens include those proteins discussed above. Preferred molecular targets for antibodies encompassed by the present invention include CD polypeptides such as CD3, CD4, CD8, CD19, CD20 and CD34; members of the HER receptor family such as the EGF receptor (HER1), HER2, HER3 or HER4 receptor; cell adhesion molecules such as LFA-1, Mac1, p150,95, VLA-4, ICAM-1, VCAM and αv/b3 integrin including either a or b subunits thereof (e.g., anti-CD11a, anti-CD18 or anti-CD11b antibodies); growth factors such as VEGF; IgE; blood group antigens; flk2/flt3 receptor; obesity (OB) receptor; mpl receptor; CTLA-4; polypeptide C etc. Soluble antigens or fragments thereof, optionally conjugated to other molecules, can be used as immunogens for generating antibodies. For transmembrane molecules, such as receptors, fragments of these (e.g., the extracellular domain of a receptor) can be used as the immunogen. Alternatively, cells expressing the transmembrane molecule can be used as the immunogen. Such cells can be derived from a natural source (e.g., cancer cell lines) or may be cells which have been transformed by recombinant techniques to express the transmembrane molecule.

Examples of antibodies to be purified herein include, but are not limited to: HER2 antibodies including trastuzumab (HERCEPTIN®) (Carter et al., *Proc. Natl. Acad. Sci. USA*, 89:4285-4289 (1992), U.S. Pat. No. 5,725,856) and pertuzumab (OMNITARGT™) (WO01/00245); CD20 antibodies (see below); IL-8 antibodies (St John et al., *Chest*, 103:932 (1993), and International Publication No. WO 95/23865); VEGF or VEGF receptor antibodies including humanized and/or affinity matured VEGF antibodies such as the humanized VEGF antibody huA4.6.1 bevacizumab (AVASTIN®) and ranibizumab (LUCENTIS®) (Kim et al., *Growth Factors*, 7:53-64 (1992), International Publication No. WO 96/30046, and WO 98/45331, published Oct. 15, 1998); PSCA antibodies (WO01/40309); CD11a antibodies including efalizumab (RAPTIVA®) (U.S. Pat. No. 6,037,454, U.S. Pat. No. 5,622,700, WO 98/23761, Stoppa et al., *Transplant Intl.* 4:3-7 (1991), and Hourmant et al., *Transplantation* 58:377-380 (1994)); antibodies that bind IgE including omalizumab (XOLAIR®) (Presta et al., *J. Immunol.* 151:2623-2632 (1993), and International Publication No. WO 95/19181;U.S. Pat. No. 5,714,338, issued Feb. 3, 1998 or U.S. Pat. No. 5,091,313, issued Feb. 25, 1992, WO 93/04173 published Mar. 4, 1993, or International Application No. PCT/US98/13410 filed Jun. 30, 1998, U.S. Pat. No. 5,714,338); CD18 antibodies (U.S. Pat. No. 5,622,700, issued Apr. 22, 1997, or as in WO 97/26912, published Jul. 31, 1997); Apo-2 receptor antibody antibodies (WO 98/51793 published Nov. 19, 1998); Tissue Factor (TF) antibodies (European Patent No. 0 420 937 B1 granted Nov. 9, 1994); $\alpha_4$-$\alpha_7$ integrin antibodies (WO 98/06248 published Feb. 19, 1998); EGFR antibodies (e.g., chimerized or humanized 225 antibody, cetuximab, ERBUTIX® as in WO 96/40210 published Dec. 19, 1996); CD3 antibodies such as OKT3 (U.S. Pat. No.

4,515,893 issued May 7, 1985); CD25 or Tac antibodies such as CHI-621 (SIMULECT®) and ZENAPAX® (See U.S. Pat. No. 5,693,762 issued Dec. 2, 1997); CD4 antibodies such as the cM-7412 antibody (Choy et al., *Arthritis Rheum* 39(1): 52-56 (1996)); CD52 antibodies such as CAMPATH-1H (ILEX/Berlex) (Riechmann et al., *Nature* 332:323-337 (1988)); Fc receptor antibodies such as the M22 antibody directed against Fc(RI as in Graziano et al., *J. Immunol.* 155(10):4996-5002 (1995)); carcinoembryonic antigen (CEA) antibodies such as hMN-14 (Sharkey et al., *Cancer Res.* 55(23Suppl): 5935s-5945s (1995)); antibodies directed against breast epithelial cells including huBrE-3, hu-Mc 3 and CHL6 (Ceriani et al., *Cancer Res.* 55(23): 5852s-5856s (1995); and Richman et al., *Cancer Res.* 55(23 Supp): 5916s-5920s (1995)); antibodies that bind to colon carcinoma cells such as C242 (Litton et al., *Eur J. Immunol.* 26(1):1-9 (1996)); CD38 antibodies, e.g., AT 13/5 (Ellis et al., *J. Immunol.* 155(2):925-937 (1995)); CD33 antibodies such as Hu M195 (Jurcic et al., *Cancer Res* 55(23 Suppl):5908s-5910s (1995)) and CMA-676 or CDP771; EpCAM antibodies such as 17-1A (PANOREX®); GpIIb/IIIa antibodies such as abciximab or c7E3 Fab (REOPRO®); RSV antibodies such as MEDI-493 (SYNAGIS®); CMV antibodies such as PROTOVIR®; HIV antibodies such as PRO542; hepatitis antibodies such as the Hep B antibody OSTAVIR®; CA125 antibody including anti-MUC16 (WO2007/001851; Yin, B W T and Lloyd, K O, *J. Biol. Chem.* 276:27371-27375 (2001)) and OvaRex; idiotypic GD3 epitope antibody BEC2; αvβ3 antibody (e.g., VITAXIN®; Medimmune); human renal cell carcinoma antibody such as ch-G250; ING-1; anti-human 17-1An antibody (3622W94); anti-human colorectal tumor antibody (A33); anti-human melanoma antibody R24 directed against GD3 ganglioside; anti-human squamous-cell carcinoma (SF-25); human leukocyte antigen (HLA) antibody such as Smart ID10 and the anti-HLA DR antibody Oncolym (Lym-1); CD37 antibody such as TRU 016 (Trubion); IL-21 antibody (Zymogenetics/Novo Nordisk); anti-B cell antibody (Impheron); B cell targeting MAb (Immunogen/Aventis); 1D09C3 (Morphosys/GPC); LymphoRad 131 (HGS); Lym-1 antibody, such as Lym-1Y-90 (USC) or anti-Lym-1 Oncolym (USC/Peregrine); LIF 226 (Enhanced Lifesci.); BAFF antibody (e.g., WO 03/33658); BAFF receptor antibody (see e.g., WO 02/24909); BR3 antibody; Blys antibody such as belimumab; LYMPHOSTAT-B™; ISF 154 (UCSD/Roche/Tragen); gomiliximab (Idec 152; Biogen Idec); IL-6 receptor antibody such as atlizumab (ACTEMRA™; Chugai/Roche); IL-15 antibody such as HuMax-11-15 (Genmab/Amgen); chemokine receptor antibody, such as a CCR2 antibody (e.g., MLN1202; Millieneum); anti-complement antibody, such as C5 antibody (e.g., eculizumab, 5G1.1; Alexion); oral formulation of human immunoglobulin (e.g., IgPO; Protein Therapeutics); IL-12 antibody such as ABT-874 (CAT/Abbott); Teneliximab (BMS-224818; BMS); CD40 antibodies, including S2C6 and humanized variants thereof (WO00/75348) and TNX 100 (Chiron/Tanox); TNF-α antibodies including cA2 or infliximab (REMICADE®), CDP571, MAK-195, adalimumab (HUMIRAT™), pegylated TNF-α antibody fragment such as CDP-870 (Celltech), D2E7 (Knoll), anti-TNF-α polyclonal antibody (e.g., PassTNF; Verigen); CD22 antibodies such as LL2 or epratuzumab (LYMPHOCIDE®; Immunomedics), including epratuzumab Y-90 and epratzumab I-131, Abiogen's CD22 antibody (Abiogen, Italy), CMC 544 (Wyeth/Celltech), combotox (UT Soutwestern), BL22 (NIH), and LympoScan Tc99 (Immunomedics).

Examples of CD20 antibodies include: "C2B8," which is now called "rituximab" ("RITUXAN®") (U.S. Pat. No. 5,736,137); the yttrium-[90]-labelled 2B8 murine antibody designated "Y2B8" or "Ibritumomab Tiuxetan" (ZEVALIN®) commercially available from IDEC Pharmaceuticals, Inc. (U.S. Pat. No. 5,736,137; 2B8 deposited with ATCC under accession no. HB11388 on Jun. 22, 1993); murine IgG2a "B1," also called "Tositumomab," optionally labelled with $^{131}$I to generate the "131I-B1" or "iodine 1131 tositumomab" antibody (BEXXAR™) commercially available from Corixa (see, also, U.S. Pat. No. 5,595,721); murine monoclonal antibody "1F5" (Press et al., *Blood* 69(2):584-591 (1987)) and variants thereof including "framework patched" or humanized 1F5 (WO 2003/002607, Leung, S.; ATCC deposit HB-96450); murine 2H7 and chimeric 2H7 antibody (U.S. Pat. No. 5,677,180); humanized 2H7 (WO 2004/056312, Lowman et al.); 2F2 (HuMax-CD20), a fully human, high-affinity antibody targeted at the CD20 molecule in the cell membrane of B-cells (Genmab, Denmark; see, for example, Glennie and van de Winkel, *Drug Discovery Today* 8: 503-510 (2003) and Cragg et al., *Blood* 101: 1045-1052 (2003); WO 2004/035607; US2004/0167319); the human monoclonal antibodies set forth in WO 2004/035607 and US2004/0167319 (Teeling et al.); the antibodies having complex N-glycoside-linked sugar chains bound to the Fc region described in US 2004/0093621 (Shitara et al.); monoclonal antibodies and antigen-binding fragments binding to CD20 (WO 2005/000901, Tedder et al.,) such as HB20-3, HB20-4, HB20-25, and MB20-11; CD20 binding molecules such as the AME series of antibodies, e.g., AME 33 antibodies as set forth in WO 2004/103404 and US2005/0025764 (Watkins et al., Eli Lilly/Applied Molecular Evolution, AME); CD20 binding molecules such as those described in US 2005/0025764 (Watkins et al.); A20 antibody or variants thereof such as chimeric or humanized A20 antibody (cA20, hA20, respectively) or IMMU-106 (US 2003/0219433, Immunomedics); CD20-binding antibodies, including epitope-depleted Leu-16, 1H4, or 2B8, optionally conjugated with IL-2, as in US 2005/0069545A1 and WO 2005/16969 (Carr et al.); bispecific antibody that binds CD22 and CD20, for example, hLL2xhA20 (WO2005/14618, Chang et al.); monoclonal antibodies L27, G28-2, 93-1B3, B-C1 or NU-B2 available from the International Leukocyte Typing Workshop (Valentine et al., In: *Leukocyte Typing* III (McMichael, Ed., p. 440, Oxford University Press (1987)); 1H4 (Haisma et al., *Blood* 92:184 (1998)); anti-CD20 auristatin E conjugate (Seattle Genetics); anti-CD20-IL2 (EMD/Biovation/City of Hope); anti-CD20 MAb therapy (EpiCyte); anti-CD20 antibody TRU 015 (Trubion).

The term "antibody" as used herein includes monoclonal antibodies (including full length antibodies which have an immunoglobulin Fc region), antibody compositions with polyepitopic specificity, multispecific antibodies (e.g., bispecific antibodies, diabodies, and single-chain molecules, as well as antibody fragments (e.g., Fab, F(ab')$_2$, and Fv). The term "immunoglobulin" (Ig) is used interchangeably with "antibody" herein.

The basic 4-chain antibody unit is a heterotetrameric glycoprotein composed of two identical light (L) chains and two identical heavy (H) chains. An IgM antibody consists of 5 of the basic heterotetramer unit along with an additional polypeptide called a J chain, and contains 10 antigen binding sites, while IgA antibodies comprise from 2-5 of the basic 4-chain units which can polymerize to form polyvalent assemblages in combination with the J chain. In the case of IgGs, the 4-chain unit is generally about 150,000 daltons. Each L chain is linked to an H chain by one covalent disulfide bond, while the two H chains are linked to each other by one or more disulfide bonds depending on the H chain isotype.

Each H and L chain also has regularly spaced intrachain disulfide bridges. Each H chain has at the N-terminus, a variable domain ($V_H$) followed by three constant domains ($C_H$) for each of the α and γ chains and four $C_H$ domains for μ and ε isotypes. Each L chain has at the N-terminus, a variable domain ($V_L$) followed by a constant domain at its other end. The $V_L$ is aligned with the $V_H$ and the $C_L$ is aligned with the first constant domain of the heavy chain ($C_H1$). Particular amino acid residues are believed to form an interface between the light chain and heavy chain variable domains. The pairing of a $V_H$ and $V_L$ together forms a single antigen-binding site. For the structure and properties of the different classes of antibodies, see e.g., *Basic and Clinical Immunology*, 8th Edition, Daniel P. Sties, Abba I. Ten and Tristram G. Parsolw (eds), Appleton & Lange, Norwalk, Conn., 1994, page 71 and Chapter 6.

The L chain from any vertebrate species can be assigned to one of two clearly distinct types, called kappa and lambda, based on the amino acid sequences of their constant domains. Depending on the amino acid sequence of the constant domain of their heavy chains (CH), immunoglobulins can be assigned to different classes or isotypes. There are five classes of immunoglobulins: IgA, IgD, IgE, IgG and IgM, having heavy chains designated α, δ, ε, γ. and μ, respectively. The γ and α classes are further divided into subclasses on the basis of relatively minor differences in the CH sequence and function, e.g., humans express the following subclasses: IgG1, IgG2, IgG3, IgG4, IgA1 and IgA2.

The term "variable" refers to the fact that certain segments of the variable domains differ extensively in sequence among antibodies. The V domain mediates antigen binding and defines the specificity of a particular antibody for its particular antigen. However, the variability is not evenly distributed across the entire span of the variable domains. Instead, the V regions consist of relatively invariant stretches called framework regions (FRs) of about 15-30 amino acid residues separated by shorter regions of extreme variability called "hypervariable regions" or sometimes "complementarity determining regions" (CDRs) that are each approximately 9-12 amino acid residues in length. The variable domains of native heavy and light chains each comprise four FRs, largely adopting a β-sheet configuration, connected by three hypervariable regions, which form loops connecting, and in some cases forming part of, the β-sheet structure. The hypervariable regions in each chain are held together in close proximity by the FRs and, with the hypervariable regions from the other chain, contribute to the formation of the antigen binding site of antibodies (see Kabat et al., *Sequences of Proteins of Immunological Interest*, 5th Ed. Public Health Service, National Institutes of Health, Bethesda, Md. (1991). The constant domains are not involved directly in binding an antibody to an antigen, but exhibit various effector functions, such as participation of the antibody dependent cellular cytotoxicity (ADCC).

The term "hypervariable region" (also known as "complementarity determining regions" or CDRs) when used herein refers to the amino acid residues of an antibody which are (usually three or four short regions of extreme sequence variability) within the V-region domain of an immunoglobulin which form the antigen-binding site and are the main determinants of antigen specificity. There are at least two methods for identifying the CDR residues: (1) An approach based on cross-species sequence variability (i.e., Kabat et al., *Sequences of Proteins of Immunological Interest* (National Institute of Health, Bethesda, M S 1991); and (2) An approach based on crystallographic studies of antigen-antibody complexes (Chothia, C. et al., *J. Mol. Biol.* 196: 901-917 (1987)).

However, to the extent that two residue identification techniques define regions of overlapping, but not identical regions, they can be combined to define a hybrid CDR.

The term "monoclonal antibody" as used herein refers to an antibody obtained from a population of substantially homogeneous antibodies, i.e., the individual antibodies comprising the population are identical except for possible naturally occurring mutations and/or post-translation modifications (e.g., isomerizations, amidations) that may be present in minor amounts. Monoclonal antibodies are highly specific, being directed against a single antigenic site. Furthermore, in contrast to conventional (polyclonal) antibody preparations which typically include different antibodies directed against different determinants (epitopes), each monoclonal antibody is directed against a single determinant on the antigen. In addition to their specificity, the monoclonal antibodies are advantageous in that they are synthesized by the hybridoma culture, uncontaminated by other immunoglobulins. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler et al., *Nature*, 256: 495 (1975), or may be made by recombinant DNA methods (see, e.g., U.S. Pat. No. 4,816,567). The "monoclonal antibodies" may also be isolated from phage antibody libraries using the techniques described in Clackson et al., *Nature*, 352:624-628 (1991) and Marks et al., *J. Mol. Biol.*, 222:581-597 (1991), for example.

The monoclonal antibodies herein specifically include "chimeric" antibodies (immunoglobulins) in which a portion of the heavy and/or light chain is identical with or homologous to corresponding sequences in antibodies derived from a particular species or belonging to a particular antibody class or subclass, while the remainder of the chain(s) is (are) identical with or homologous to corresponding sequences in antibodies derived from another species or belonging to another antibody class or subclass, as well as fragments of such antibodies, so long as they exhibit the desired biological activity (U.S. Pat. No. 4,816,567; Morrison et al., *Proc. Natl. Acad. Sci. USA*, 81:6851-6855 (1984)). Chimeric antibodies of interest herein include "primitized" antibodies comprising variable domain antigen-binding sequences derived from a non-human primate (e.g., Old World Monkey, Ape etc.) and human content region sequences.

An "intact" antibody is one which comprises an antigen-binding site as well as a CL and at least the heavy chain domains, $C_H1$, $C_H2$ and $C_H3$. The constant domains may be native sequence constant domains (e.g., human native sequence constant domains) or amino acid sequence variants thereof. Preferably, the intact antibody has one or more effector functions.

An "antibody fragment" comprises a portion of an intact antibody, preferably the antigen binding and/or the variable region of the intact antibody. Examples of antibody fragments include Fab, Fab', F(ab')$_2$ and Fv fragments; diabodies; linear antibodies (see U.S. Pat. No. 5,641,870, Example 2; Zapata et al., *Protein Eng*. 8(10): 1057-1062 [1995]); single-chain antibody molecules and multispecific antibodies formed from antibody fragments.

Papain digestion of antibodies produced two identical antigen-binding fragments, called "Fab" fragments, and a residual "Fc" fragment, a designation reflecting the ability to crystallize readily. The Fab fragment consists of an entire L chain along with the variable region domain of the H chain ($V_H$), and the first constant domain of one heavy chain ($C_H1$). Each Fab fragment is monovalent with respect to antigen binding, i.e., it has a single antigen-binding site. Pepsin treatment of an antibody yields a single large F(ab')$_2$ fragment which roughly corresponds to two disulfide linked Fab fragments having different antigen-binding activity and is still capable of cross-linking antigen. Fab' fragments differ from Fab fragments by having a few additional residues at the carboxy terminus of the $C_H1$ domain including one or more cysteines from the antibody hinge region. Fab'-SH is the designation herein for Fab' in which the cysteine residue(s) of the constant domains bear a free thiol group. F(ab')$_2$ antibody fragments originally were produced as pairs of Fab' fragments which have hinge cysteines between them. Other chemical couplings of antibody fragments are also known.

The Fc fragment comprises the carboxy-terminal portions of both H chains held together by disulfides. The effector functions of antibodies are determined by sequences in the Fc region, the region which is also recognized by Fc receptors (FcR) found on certain types of cells.

"Fv" is the minimum antibody fragment which contains a complete antigen-recognition and -binding site. This fragment consists of a dimer of one heavy- and one light-chain variable region domain in tight, non-covalent association. From the folding of these two domains emanate six hypervarible loops (3 loops each from the H and L chain) that contribute the amino acid residues for antigen binding and confer antigen binding specificity to the antibody. However, even a single variable domain (or half of an Fv comprising only three CDRs specific for an antigen) has the ability to recognize and bind antigen, although at a lower affinity than the entire binding site.

"Single-chain Fv" also abbreviated as "sFv" or "scFv" are antibody fragments that comprise the VH and VL antibody domains connected into a single polypeptide chain. Preferably, the sFv polypeptide further comprises a polypeptide linker between the $V_H$ and $V_L$ domains which enables the sFv to form the desired structure for antigen binding. For a review of the sFv, see Pluckthun in *The Pharmacology of Monoclonal Antibodies*, vol. 113, Rosenburg and Moore eds., Springer-Verlag, New York, pp. 269-315 (1994).

The term "diabodies" refers to small antibody fragments prepared by constructing sFv fragments (see preceding paragraph) with short linkers (about 5-10) residues) between the $V_H$ and $V_L$ domains such that inter-chain but not intra-chain pairing of the V domains is achieved, thereby resulting in a bivalent fragment, i.e., a fragment having two antigen-binding sites. Bispecific diabodies are heterodimers of two "crossover" sFv fragments in which the $V_H$ and $V_L$ domains of the two antibodies are present on different polypeptide chains. Diabodies are described in greater detail in, for example, EP 404,097; WO 93/11161; Hollinger et al., *Proc. Natl. Acad. Sci. USA* 90: 6444-6448 (1993).

An antibody that "specifically binds to" or is "specific for" a particular polypeptide or an epitope on a particular polypeptide is one that binds to that particular polypeptide or epitope on a particular polypeptide without substantially binding to any other polypeptide or polypeptide epitope.

The term "solid phase" describes a non-aqueous matrix to which the antibody of the present invention can adhere. Examples of solid phases encompassed herein include those formed partially or entirely of glass (e.g., controlled pore glass), polysaccharides (e.g., agarose), polyacrylamides, polystyrene, polyvinyl alcohol and silicones. In certain embodiments, depending on the context, the solid phase can comprise the well of an assay plate; in others it is a purification column (e.g., an affinity chromatography column). This term also includes a discontinuous solid phase of discrete particles, such as those described in U.S. Pat. No. 4,275,149.

"Humanized" forms of non-human (e.g., murine) antibodies are chimeric immunoglobulins, immunoglobulin chains or fragments thereof (such as Fv, Fab, Fab', F(ab')$_2$ or other antigen-binding subsequences of antibodies) of mostly human sequences, which contain minimal sequence derived from non-human immunoglobulin. For the most part, humanized antibodies are human immunoglobulins (recipient antibody) in which residues from a hypervariable region (also CDR) of the recipient are replaced by residues from a hypervariable region of a non-human species (donor antibody) such as mouse, rat or rabbit having the desired specificity, affinity, and capacity. In some instances, Fv framework region (FR) residues of the human immunoglobulin are replaced by corresponding non-human residues. Furthermore, "humanized antibodies" as used herein may also comprise residues which are found neither in the recipient antibody nor the donor antibody. These modifications are made to further refine and optimize antibody performance. The humanized antibody optimally also will comprise at least a portion of an immunoglobulin constant region (Fc), typically that of a human immunoglobulin. For further details, see Jones et al., *Nature*, 321:522-525 (1986); Reichmann et al., *Nature*, 332:323-329 (1988); and Presta, *Curr. Op. Struct. Biol.*, 2:593-596 (1992).

A "species-dependent antibody", e.g., a mammalian anti-human IgE antibody, is an antibody which has a stronger binding affinity for an antigen from a first mammalian species than it has for a homologue of that antigen from a second mammalian species. Normally, the species-dependent antibody "bind specifically" to a human antigen (i.e., has a binding affinity (Kd) value of no more than about $1 \times 10^{-7}$ M, alternatively no more than about $1 \times 10^{-8}$ M, alternatively no more than about $1 \times 10^{-9}$ M) but has a binding affinity for a homologue of the antigen from a second non-human mammalian species which is at least about 50 fold, at least about 500 fold, or at least about 1000 fold, weaker than its binding affinity for the non-human antigen. The species-dependent antibody can be of any of the various types of antibodies as defined above, but preferably is a humanized or human antibody.

Antibody "effector functions" refer to those biological activities attributable to the Fc region (a native sequence Fc region or amino acid sequence variant Fc region) of an antibody, and vary with the antibody isotype. Examples of antibody effector functions include: C1q binding and complement dependent cytotoxicity; Fc receptor binding; antibody-dependent cell-mediated cytotoxicity (ADCC); phagocytosis; down regulation of cell surface receptors (e.g., B cell receptors); and B cell activation.

"Antibody-dependent cell-mediated cytotoxicity" or ADCC refers to a form of cytotoxicity in which secreted Ig bound onto Fc receptors (FcRs) present on certain cytotoxic cells (e.g., natural killer (NK) cells, neutrophils and macrophages) enable these cytotoxic effector cells to bind specifically to an antigen-bearing target cell and subsequently kill the target cell with cytotoxins. The antibodies "arm" the cytotoxic cells and are required for killing of the target cell by this mechanism. The primary cells for mediating ADCC, NK cells, express FcγRIII only, whereas monocytes express FcγRI, FcγRII and FcγRIII. Fc expression on hematopoietic cells is summarized in Table 3 on page 464 of Ravetch and Kinet, *Annu. Rev. Immunol.* 9: 457-92 (1991). To assess ADCC activity of a molecule of interest, an in vitro ACDD assay, such as that described in U.S. Pat. No. 5,500,362 or 5,821,337 may be performed. Useful effector cells for such assays include peripheral blood mononuclear cells (PBMC)

and natural killer (NK) cells. Alternatively, or additionally, ADCC activity of the molecule of interest may be assessed in vivo, e.g., in an animal model such as that disclosed in Clynes et al., *PNAS USA* 95:652-656 (1998).

"Fc receptor" or "FcR" describes a receptor that binds to the Fc region of an antibody. The preferred FcR is a native sequence human FcR. Moreover, a preferred FcR is one which binds an IgG antibody (a gamma receptor) and includes receptors of the FcγRI, FcγRII, and FcγRIII subclasses, including allelic variants and alternatively spliced forms of these receptors, FcγRII receptors include FcγRIIA (an "activating receptor") and FcγRIIB (an "inhibiting receptor"), which have similar amino acid sequences that differ primarily in the cytoplasmic domains thereof. Activating receptor FcγRIIA contains an immunoreceptor tyrosine-based activation motif (ITAM) in its cytoplasmic domain. Inhibiting receptor FcγRIIB contains an immunoreceptor tyrosine-based inhibition motif (ITIM) in its cytoplasmic domain. (see M. Daeron, *Annu. Rev. Immunol.* 15:203-234 (1997). FcRs are reviewed in Ravetch and Kinet, *Annu. Rev. Immunol.* 9: 457-92 (1991); Capel et al., Immunomethods 4: 25-34 (1994); and de Haas et al., *J. Lab. Clin. Med.* 126: 330-41 (1995). Other FcRs, including those to be identified in the future, are encompassed by the term "FcR" herein. The term also includes the neonatal receptor, FcRn, which is responsible for the transfer of maternal IgGs to the fetus. Guyer et al., *J. Immunol.* 117: 587 (1976) and Kim et al., *J. Immunol.* 24: 249 (1994).

"Human effector cells" are leukocytes which express one or more FcRs and perform effector functions. Preferably, the cells express at least FcγRIII and perform ADCC effector function. Examples of human leukocytes which mediate ADCC include peripheral blood mononuclear cells (PBMC), natural killer (NK) cells, monocytes, cytotoxic T cells and neutrophils, with PBMCs and MNK cells being preferred. The effector cells may be isolated from a native source, e.g., blood.

"Complement dependent cytotoxicity" of "CDC" refers to the lysis of a target cell in the presence of complement. Activation of the classical complement pathway is initiated by the binding of the first component of the complement system (C1q) to antibodies (of the appropriate subclass) which are bound to their cognate antigen. To assess complement activation, a CDC assay, e.g., as described in Gazzano-Santoro et al., *J. Immunol. Methods* 202: 163 (1996), may be performed.

The term "pharmaceutical formulation" refers to a preparation which is in such form as to permit the biological activity of the active ingredient to be effective, and which contains no additional components which are unacceptably toxic to a subject to which the formulation would be administered.

An antibody possesses "biological activity" in a pharmaceutical formulation, if the biological activity of the antibody at a given time is within about 10% (within the errors of the assay) of the biological activity exhibited at the time the pharmaceutical formulation was prepared, as determined by the ability of the antibody in vitro or in vivo to bind to antigen and result in a measurable biological response.

A "stable" formulation is one in which the protein therein essentially retains its physical and/or chemical stability upon storage. Stability can be measured at a selected temperature for a selected time period. Preferably, the formulation is stable at room temperature (~30° C.) or at 40° C. for at least 1 month and/or stable at about 2-8° C. for at least 1 year and preferably for at least 2 years. For example, the extent of aggregation during storage can be used as an indicator of protein stability. Thus, a "stable" formulation may be one wherein less than about 10% and preferably less than about 5% of the protein is present as an aggregate in the formulation. Various analytical techniques for measuring protein stability are available in the art and are reviewed, for example, in *Peptide and Protein Drug Delivery*, 247-301, Vincent Lee Ed., Marcel Dekker, Inc., New York, N.Y., Pubs. (1991) and Jones, A. *Adv. Drug Delivery Rev.* 10: 29-90 (1993).

Increasing the "stability" of a protein-containing formulation refers to reducing (as compared to an untreated protein-containing formulation) or preventing the formation of protein aggregates in that formulation.

The term "aqueous solution" refers to a solution in which water is the dissolving medium or solvent. When a substance dissolves in a liquid, the mixture is termed a solution. The dissolved substance is the solute, and the liquid that does the dissolving (in this case water) is the solvent.

The term, "stabilizing agent" or "stabilizer" as used herein is a chemical or compound that is added to a solution or mixture or suspension or composition or therapeutic composition to maintain it in a stable or unchanging state; or is one which is used because it produces a reaction involving changes in atoms or molecules leading to a more stable or unchanging state.

The term "aggregate" or "aggregation" as used herein is means to come together or collect in a mass or whole, e.g., as in the aggregation of peptides, polypeptides, antibodies or variants thereof. Aggregates can be self-aggregating or aggregate due to other factors, e.g., aggregating agents, precipitating agents, agitation, or other means and methods whereby peptides, polypeptides, antibodies or variants thereof cause to come together.

Agitation-induced aggregation is formation of aggregates in a protein-containing solution induced by agitation, where agitation is putting into motion by shaking or stirring.

An antibody that is "susceptible to aggregation" is one that has been observed to aggregate with other antibody molecule(s), especially upon agitation.

By "inhibiting" agitation-induced aggregation is intended preventing, reducing, or decreasing the amount of agitation-induced aggregation, measured by comparing the amount of aggregate present in a protein-containing solution that comprises at least one inhibitor of agitation-induced aggregation with the amount of aggregate present in a protein-containing solution that does not comprise at least one inhibitor of agitation-induced aggregation.

An "agitation-induced aggregation inhibiting" amount of an alkylglycoside is the amount of that alkylglycoside that detectably inhibits agitation-induced aggregation of a protein as compared to an identically treated protein in the absence of the alkylglycoside.

An "oxidized" protein herein is one in which one or more amino acid residue(s) thereof has been oxidized. In certain embodiments, the oxidized amino acid is tryptophan. Oxidation of amino acids in proteins may be induced by exposure to light which is, therefore, referred to herein as "light-induced oxidation".

A protein that is "susceptible to oxidation" is one comprising one or more residue(s) that has been found to be prone to oxidation.

By "inhibiting" or "preventing" oxidation it is intended as reducing or decreasing the amount of oxidation, measured by comparing the amount of oxidation present in a protein-containing solution that comprises at least one inhibitor of oxidation with the amount of oxidation present in a protein-containing solution that does not comprise at least one inhibitor of oxidation.

An "oxidation preventing" amount of an alkylglycoside is the amount of that alkylglycoside that detectably inhibits or reduces oxidation of a protein as compared to an identically treated protein in the absence of the alkylglycoside.

Methods which may find use in the present invention for measuring agitation-induced aggregation and/or protein oxidation include gel electrophoresis, isoelectric focusing, capillary electrophoresis, chromatography such as size exclusion chromatography, ion-exchange chromatography, and reversed-phase high performance liquid chromatography, peptide mapping, oligosaccharide mapping, mass spectrometry, ultraviolet absorbance spectroscopy, fluorescence spectroscopy, circular dichroism spectroscopy, isothermal titration calorimetry, differential scanning calorimetry, analytical ultra-centrifugation, dynamic light scattering, proteolysis, and cross-linking, turbidity measurement, filter retardation assays, immunological assays, fluorescent dye binding assays, protein-staining assays, microscopy, and detection of aggregates via ELISA or other binding assay.

The "critical micelle concentration" (CMC) is the threshold concentration at which a surfactant aggregates in solution to form clusters called micelles. As used herein, CMC values for any particular surfactant are measured at 20-25° C. in water, preferably at 25° C. in water, and may be expressed in units of mM or w/v. Because the formation of micelles from constituent monomers involves an equilibrium, the existence of a narrow concentration range for micelles, below which the solution contains negligible amounts of micelles and above which practically all additional surfactant is found in the form of additional micelles, has been established. A compilation of CMCs for hundreds of compounds in aqueous solution has been prepared by Mukerjee, P. and Mysels, K. J. (1971) Critical Micelle Concentrations of Aqueous Surfactant Systems, NSRDS-NBS 36. Superintendent of Documents, U.S. Government Printing Office, Washington, D.C. See also, http://www.anatrace.com/docs/detergent_data.pdf.

One common technique used to determine CMC is direct measurement of equilibrium surface tension as function of surfactant concentration using a surface tensiometer. Other methods include measuring intensity of scattered light, solubilization of fluorescent dyes, etc., as a function of the surfactant concentration. These, and other such techniques are well known in the art and are routinely employed.

"Isolated" when used to describe the various polypeptides and antibodies disclosed herein, means a polypeptide or antibody that has been identified, separated and/or recovered from a component of its production environment. Preferably, the isolated polypeptide is free of association with all other components from its production environment. Contaminant components of its production environment, such as that resulting from recombinant transfected cells, are materials that would typically interfere with diagnostic or therapeutic uses for the polypeptide, and may include enzymes, hormones, and other proteinaceous or non-proteinaceous solutes. In preferred embodiments, the polypeptide will be purified (1) to a degree sufficient to obtain at least 15 residues of N-terminal or internal amino acid sequence by use of a spinning cup sequenator, or (2) to homogeneity by SDS-PAGE under non-reducing or reducing conditions using Coomassie blue or, preferably, silver stain. Ordinarily, however, an isolated polypeptide or antibody will be prepared by at least one purification step.

An "isolated" nucleic acid molecule encoding the polypeptides and antibodies herein is a nucleic acid molecule that is identified and separated from at least one contaminant nucleic acid molecule with which it is ordinarily associated in the environment in which it was produced. Preferably, the isolated nucleic acid is free of association with all components associated with the production environment. The isolated nucleic acid molecules encoding the polypeptides and antibodies herein is in a form other than in the form or setting in which it is found in nature. Isolated nucleic acid molecules therefore are distinguished from nucleic acid encoding the polypeptides and antibodies herein existing naturally in cells.

The term "control sequences" refers to DNA sequences necessary for the expression of an operably linked coding sequence in a particular host organism. The control sequences that are suitable for prokaryotes, for example, include a promoter, optionally an operator sequence, and a ribosome binding site. Eukaryotic cells are known to utilize promoters, polyadenylation signals, and enhancers.

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

The term "epitope tagged" when used herein refers to a chimeric polypeptide comprising a polypeptide or antibody described herein fused to a "tag polypeptide". The tag polypeptide has enough residues to provide an epitope against which an antibody can be made, yet is short enough such that it does not interfere with activity of the polypeptide to which it is fused. The tag polypeptide preferably also is fairly unique so that the antibody does not substantially cross-react with other epitopes. Suitable tag polypeptides generally have at least six amino acid residues and usually between about 8 and 50 amino acid residues (preferably, between about 10 and 20 amino acid residues).

As used herein, the term "immunoadhesin" designates antibody-like molecules which combine the binding specificity of a heterologous protein (an "adhesin") with the effector functions of immunoglobulin constant domains. Structurally, the immunoadhesins comprise a fusion of an amino acid sequence with the desired binding specificity which is other than the antigen recognition and binding site of an antibody (i.e., is "heterologous"), and an immunoglobulin constant domain sequence. The adhesin part of an immunoadhesin molecule typically is a contiguous amino acid sequence comprising at least the binding site of a receptor or a ligand. The immunoglobulin constant domain sequence in the immunoadhesin may be obtained from any immunoglobulin, such as IgG-1, IgG-2, IgG-3, or IgG-4 subtypes, IgA (including IgA-1 and IgA-2), IgE, IgD or IgM. The Ig fusions preferably include the substitution of a domain of a polypeptide or antibody described herein in the place of at least one variable region within an Ig molecule. In a particularly preferred embodiment, the immunoglobulin fusion includes the hinge, CH2 and CH3, or the hinge, CH1, CH2 and CH3 regions of an IgG1 molecule. For the production of immunoglobulin fusions see also U.S. Pat. No. 5,428,130 issued Jun. 27, 1995.

An "isotonic" formulation is one which has essentially the same osmotic pressure as human blood. Isotonic formulations will generally have an osmotic pressure from about 250 to 350 mOsm. The term "hypotonic" describes a formulation with an osmotic pressure below that of human blood. Correspondingly, the term "hypertonic" is used to describe a formulation with an osmotic pressure above that of human blood. Isotonicity can be measured using a vapor pressure or ice-freezing type osmometer, for example. The formulations of the present invention are hypertonic as a result of the addition of salt and/or buffer.

A "reconstituted" formulation is one which has been prepared by dissolving a lyophilized protein or antibody formulation in a diluent such that the protein is dispersed in the reconstituted formulation. The reconstituted formulation is suitable for administration (e.g., parenteral administration) to a patient to be treated with the protein of interest and, in certain embodiments of the invention, may be one which is suitable for subcutaneous administration.

A "pharmaceutically acceptable acid" includes inorganic and organic acids which are non toxic at the concentration and manner in which they are formulated. For example, suitable inorganic acids include hydrochloric, perchloric, hydrobromic, hydroiodic, nitric, sulfuric, sulfonic, sulfinic, sulfanilic, phosphoric, carbonic, etc. Suitable organic acids include straight and branched-chain alkyl, aromatic, cyclic, cyloaliphatic, arylaliphatic, heterocyclic, saturated, unsaturated, mono, di- and tri-carboxylic, including for example, formic, acetic, 2-hydroxyacetic, trifluoroacetic, phenylacetic, trimethylacetic, t-butyl acetic, anthranilic, propanoic, 2-hydroxypropanoic, 2-oxopropanoic, propandioic, cyclopentanepropionic, cyclopentane propionic, 3-phenylpropionic, butanoic, butandioic, benzoic, 3-(4-hydroxybenzoyl)benzoic, 2-acetoxy-benzoic, ascorbic, cinnamic, lauryl sulfuric, stearic, muconic, mandelic, succinic, embonic, fumaric, malic, maleic, hydroxymaleic, malonic, lactic, citric, tartaric, glycolic, glyconic, gluconic, pyruvic, glyoxalic, oxalic, mesylic, succinic, salicylic, phthalic, palmoic, palmeic, thiocyanic, methanesulphonic, ethanesulphonic, 1,2-ethanedisulfonic, 2-hydroxyethanesulfonic, benzenesulphonic, 4-chorobenzenesulfonic, napthalene-2-sulphonic, p-toluenesulphonic, camphorsulphonic, 4-methylbicyclo[2.2.2]-oct-2-ene-1-carboxylic, glucoheptonic, 4,4'-methylenebis-3-(hydroxy-2-ene-1-carboxylic acid), hydroxynapthoic.

"Pharmaceutically-acceptable bases" include inorganic and organic bases which are non-toxic at the concentration and manner in which they are formulated. For example, suitable bases include those formed from inorganic base forming metals such as lithium, sodium, potassium, magnesium, calcium, ammonium, iron, zinc, copper, manganese, aluminum, N-methylglucamine, morpholine, piperidine and organic nontoxic bases including, primary, secondary and tertiary amine, substituted amines, cyclic amines and basic ion exchange resins, [e.g., $N(R')_4+$ (where R' is independently H or $C_{1-4}$ alkyl, e.g., ammonium, Tris)], for example, isopropylamine, trimethylamine, diethylamine, triethylamine, tripropylamine, ethanolamine, 2-diethyl amino ethanol, trimethamine, dicyclohexylamine, lysine, arginine, histidine, caffeine, procaine, hydrabamine, choline, betaine, ethylenediamine, glucosamine, methylglucamine, theobromine, purines, piperazine, piperidine, N-ethylpiperidine, polyamine resins and the like. Particularly preferred organic non-toxic bases are isopropylamine, diethylamine, ethanolamine, trimethamine, dicyclohexylamine, choline, and caffeine.

Additional pharmaceutically acceptable acids and bases useable with the present invention include those which are derived from the amino acids, for example, histidine, glycine, phenylalanine, aspartic acid, glutamic acid, lysine and asparagine.

"Pharmaceutically acceptable" buffers and salts include those derived from both acid and base addition salts of the above indicated acids and bases. Specific buffers and/or salts include histidine, succinate and acetate.

A "lyoprotectant" is a molecule which, when combined with a protein of interest, significantly prevents or reduces physicochemical instability of the protein upon lyophilization and subsequent storage. Exemplary lyoprotectants include sugars and their corresponding sugar alcohols; an amino acid such as monosodium glutamate or histidine; a methylamine such as betaine; a lyotropic salt such as magnesium sulfate; a polyol such as trihydric or higher molecular weight sugar alcohols, e.g., glycerin, dextran, erythritol, glycerol, arabitol, xylitol, sorbitol, and mannitol; propylene glycol; polyethylene glycol; Pluronics®; and combinations thereof. Additional exemplary lyoprotectants include glycerin and gelatin, and the sugars mellibiose, melezitose, raffinose, mannotriose and stachyose. Examples of reducing sugars include glucose, maltose, lactose, maltulose, iso-maltulose and lactulose. Examples of non-reducing sugars include non-reducing glycosides of polyhydroxy compounds selected from sugar alcohols and other straight chain polyalcohols. Preferred sugar alcohols are monoglycosides, especially those compounds obtained by reduction of disaccharides such as lactose, maltose, lactulose and maltulose. The glycosidic side group can be either glucosidic or galactosidic. Additional examples of sugar alcohols are glucitol, maltitol, lactitol and iso-maltulose. The preferred lyoprotectant are the non-reducing sugars trehalose or sucrose.

The lyoprotectant is added to the pre-lyophilized formulation in a "lyoprotecting amount" which means that, following lyophilization of the protein in the presence of the lyoprotecting amount of the lyoprotectant, the protein essentially retains its physicochemical stability upon lyophilization and storage.

A "pharmaceutically acceptable sugar" is a molecule which, when combined with a protein of interest, significantly prevents or reduces physicochemical instability of the protein upon storage. When the formulation is intended to be lyophilized and then reconstituted, "pharmaceutically acceptable sugars" may also be known as a "lyoprotectant". Exemplary sugars and their corresponding sugar alcohols includes: an amino acid such as monosodium glutamate or histidine; a methylamine such as betaine; a lyotropic salt such as magnesium sulfate; a polyol such as trihydric or higher molecular weight sugar alcohols, e.g., glycerin, dextran, erythritol, glycerol, arabitol, xylitol, sorbitol, and mannitol; propylene glycol; polyethylene glycol; Pluronics®; and combinations thereof. Additional exemplary lyoprotectants include glycerin and gelatin, and the sugars mellibiose, melezitose, raffinose, mannotriose and stachyose. Examples of reducing sugars include glucose, maltose, lactose, maltulose, iso-maltulose and lactulose. Examples of non-reducing sugars include non-reducing glycosides of polyhydroxy compounds selected from sugar alcohols and other straight chain polyalcohols. Preferred sugar alcohols are monoglycosides, especially those compounds obtained by reduction of disaccharides such as lactose, maltose, lactulose and maltulose. The glycosidic side group can be either glucosidic or galactosidic. Additional examples of sugar alcohols are glucitol, maltitol, lactitol and iso-maltulose. The preferred pharmaceutically-acceptable sugars are the non-reducing sugars trehalose or sucrose.

Pharmaceutically acceptable sugars are added to the formulation in a "protecting amount" (e.g., pre-lyophilization) which means that the protein essentially retains its physicochemical stability during storage (e.g., after reconstitution and storage).

The "diluent" of interest herein is one which is pharmaceutically acceptable (safe and non-toxic for administration to a human) and is useful for the preparation of a liquid formulation, such as a formulation reconstituted after lyophilization. Exemplary diluents include sterile water, bacteriostatic water for injection (BWFI), a pH buffered solution (e.g., phosphate-buffered saline), sterile saline solution, Ringer's solution or dextrose solution. In an alternative embodiment, diluents can include aqueous solutions of salts and/or buffers.

A "preservative" is a compound which can be added to the formulations herein to reduce bacterial activity. The addition of a preservative may, for example, facilitate the production of a multi-use (multiple-dose) formulation. Examples of potential preservatives include octadecyldimethylbenzyl ammonium chloride, hexamethonium chloride, benzalkonium chloride (a mixture of alkylbenzyldimethylammonium chlorides in which the alkyl groups are long-chain compounds), and benzethonium chloride. Other types of preservatives include aromatic alcohols such as phenol, butyl and benzyl alcohol, alkyl parabens such as methyl or propyl paraben, catechol, resorcinol, cyclohexanol, 3-pentanol, and m-cresol. The most preferred preservative herein is benzyl alcohol.

"Treatment" refers to both therapeutic treatment and prophylactic or preventative measures. Those in need of treatment include those already with the disorder as well as those in which the disorder is to be prevented.

"Mammal" for purposes of treatment refers to any animal classified as a mammal, including humans, domestic and farm animals, and zoo, sports, or pet animals, such as dogs, horses, rabbits, cattle, pigs, hamsters, gerbils, mice, ferrets, rats, cats, etc. Preferably, the mammal is human.

A "disorder" is any condition that would benefit from treatment with the protein. This includes chronic and acute disorders or diseases including those pathological conditions which predispose the mammal to the disorder in question. Non-limiting examples of disorders to be treated herein include carcinomas and inflammations.

A "therapeutically effective amount" is at least the minimum concentration required to effect a measurable improvement or prevention of a particular disorder. Therapeutically effective amounts of known proteins are well known in the art, while the effective amounts of proteins hereinafter discovered may be determined by standard techniques which are well within the skill of a skilled artisan, such as an ordinary physician.

Methods for the preparation of antibodies (including antibodies that are conjugated to a toxin) and other proteins which may be formulated as described herein are well known in the art and are described in detail in, for example, WO2007/001851.

Antibodies and other proteins may be formulated in accordance with the present invention in either aqueous or lyophilized form, the latter being capable if being reconstituted into an aqueous form.

The formulations described herein may be prepared as reconstituted lyophilized formulations. The proteins or antibodies described herein are lyophilized and then reconstituted to produce the liquid formulations of the invention. In this particular embodiment, after preparation of the protein of interest as described above, a "pre-lyophilized formulation" is produced. The amount of protein present in the pre-lyophilized formulation is determined taking into account the desired dose volumes, mode(s) of administration etc. For example, the starting concentration of an intact antibody can be from about 2 mg/ml to about 50 mg/ml, preferably from about 5 mg/ml to about 40 mg/ml and most preferably from about 20-30 mg/ml.

The protein to be formulated is generally present in solution. For example, in the liquid formulations of the invention, the protein may be present in a pH-buffered solution at a pH from about 4-8, and preferably from about 5-7. The buffer concentration can be from about 1 mM to about 20 mM, alternatively from about 3 mM to about 15 mM, depending, for example, on the buffer and the desired tonicity of the formulation (e.g., of the reconstituted formulation). Exemplary buffers and/or salts are those which are pharmaceutically acceptable and may be created from suitable acids, bases and salts thereof, such as those which are defined under "pharmaceutically acceptable" acids, bases or buffers.

In one embodiment, a lyoprotectant is added to the pre-lyophilized formulation. The amount of lyoprotectant in the pre-lyophilized formulation is generally such that, upon reconstitution, the resulting formulation will be isotonic. However, hypertonic reconstituted formulations may also be suitable. In addition, the amount of lyoprotectant must not be too low such that an unacceptable amount of degradation/aggregation of the protein occurs upon lyophilization. However, exemplary lyoprotectant concentrations in the pre-lyophilized formulation are from about 10 mM to about 400 mM, alternatively from about 30 mM to about 300 mM, alternatively from about 50 mM to about 100 mM. Exemplary lyoprotectants include sugars and sugar alcohols such as sucrose, mannose, trehalose, glucose, sorbitol, mannitol. However, under particular circumstances, certain lyoprotectants may also contribute to an increase in viscosity of the formulation. As such, care should be taken so as to select particular lyoprotectants which minimize or neutralize this effect. Additional lyoprotectants are described above under the definition of "lyoprotectants", also referred herein as "pharmaceutically-acceptable sugars".

The ratio of protein to lyoprotectant can vary for each particular protein or antibody and lyoprotectant combination. In the case of an antibody as the protein of choice and a sugar (e.g., sucrose or trehalose) as the lyoprotectant for generating an isotonic reconstituted formulation with a high protein concentration, the molar ratio of lyoprotectant to antibody may be from about 100 to about 1500 moles lyoprotectant to 1 mole antibody, and preferably from about 200 to about 1000 moles of lyoprotectant to 1 mole antibody, for example from about 200 to about 600 moles of lyoprotectant to 1 mole antibody.

A mixture of the lyoprotectant (such as sucrose or trehalose) and a bulking agent (e.g., mannitol or glycine) may be used in the preparation of the pre-lyophilization formulation. The bulking agent may allow for the production of a uniform lyophilized cake without excessive pockets therein etc. Other pharmaceutically acceptable carriers, excipients or stabilizers such as those described in *Remington's Pharmaceutical Sciences* 16th edition, Osol, A. Ed. (1980) may be included in the pre-lyophilized formulation (and/or the lyophilized formulation and/or the reconstituted formulation) provided that they do not adversely affect the desired characteristics of the formulation. Acceptable carriers, excipients or stabilizers are nontoxic to recipients at the dosages and concentrations employed and include; additional buffering agents; preservatives; co-solvents; antioxidants including ascorbic acid and methionine; chelating agents such as EDTA; metal complexes (e.g., Zn-protein complexes); biodegradable polymers such as polyesters; and/or salt-forming counterions such as sodium.

The formulation herein may also contain more than one protein as necessary for the particular indication being treated, preferably those with complementary activities that do not adversely affect the other protein. For example, it may be desirable to provide two or more antibodies which bind to the desired target (e.g., receptor or antigen) in a single formulation. Such proteins are suitably present in combination in amounts that are effective for the purpose intended.

The formulations to be used for in vivo administration must be sterile. This is readily accomplished by filtration through sterile filtration membranes, prior to, or following, lyophilization and reconstitution. Alternatively, sterility of the entire mixture may be accomplished by autoclaving the ingredients, except for protein, at about 120° C. for about 30 minutes, for example.

After the protein, optional lyoprotectant and other optional components are mixed together, the formulation is lyophilized. Many different freeze-dryers are available for this purpose such as Hu1150™ (Hull, USA) or GT20™ (Leybold-Heraeus, Germany) freeze-dryers. Freeze-drying is accomplished by freezing the formulation and subsequently subliming ice from the frozen content at a temperature suitable for primary drying. Under this condition, the product temperature is below the eutectic point or the collapse temperature of the formulation. Typically, the shelf temperature for the primary drying will range from about −30 to 25° C. (provided the product remains frozen during primary drying) at a suitable pressure, ranging typically from about 50 to 250 mTorr. The formulation, size and type of the container holding the sample (e.g., glass vial) and the volume of liquid will mainly dictate the time required for drying, which can range from a few hours to several days (e.g., 40-60 hrs). Optionally, a secondary drying stage may also be performed depending upon the desired residual moisture level in the product. The temperature at which the secondary drying is carried out ranges from about 0-40° C., depending primarily on the type and size of container and the type of protein employed. For example, the shelf temperature throughout the entire water removal phase of lyophilization may be from about 15-30° C. (e.g., about 20° C.). The time and pressure required for secondary drying will be that which produces a suitable lyophilized cake, dependent, e.g., on the temperature and other parameters. The secondary drying time is dictated by the desired residual moisture level in the product and typically takes at least about 5 hours (e.g., 10-15 hours). The pressure may be the same as that employed during the primary drying step. Freeze-drying conditions can be varied depending on the formulation and vial size.

Prior to administration to the patient, the lyophilized formulation is reconstituted with a pharmaceutically acceptable diluent such that the protein concentration in the reconstituted formulation is at least about 50 mg/ml, for example from about 50 mg/ml to about 400 mg/ml, alternatively from about 80 mg/ml to about 300 mg/ml, alternatively from about 90 mg/ml to about 150 mg/ml. Such high protein concentrations in the reconstituted formulation are considered to be particularly useful where subcutaneous delivery of the reconstituted formulation is intended. However, for other routes of administration, such as intravenous administration, lower concentrations of the protein in the reconstituted formulation may be desired (for example from about 5-50 mg/ml, or from about 10-40 mg/ml protein in the reconstituted formulation). In certain embodiments, the protein concentration in the reconstituted formulation is significantly higher than that in the pre-lyophilized formulation. For example, the protein concentration in the reconstituted formulation may be about 2-40 times, alternatively 3-10 times, alternatively 3-6 times (e.g., at least three fold or at least four fold) that of the pre-lyophilized formulation.

Reconstitution generally takes place at a temperature of about 25° C. to ensure complete hydration, although other temperatures may be employed as desired. The time required for reconstitution will depend, e.g., on the type of diluent, amount of excipient(s) and protein. Exemplary diluents include sterile water, bacteriostatic water for injection (BWF), a pH buffered solution (e.g., phosphate-buffered saline), sterile saline solution, Ringer's solution or dextrose solution. The diluent optionally contains a preservative. Exemplary preservatives have been described above, with aromatic alcohols such as benzyl or phenol alcohol being the preferred preservatives. The amount of preservative employed is determined by assessing different preservative concentrations for compatibility with the protein and preservative efficacy testing. For example, if the preservative is an aromatic alcohol (such as benzyl alcohol), it can be present in an amount from about 0.1-2.0% and preferably from about 0.5-1.5%, but most preferably about 1.0-1.2%.

Preferably, the reconstituted formulation has less than 6000 particles per vial which are ≥10 μm in size.

Therapeutic formulations are prepared for storage by mixing the active ingredient having the desired degree of purity with optional pharmaceutically acceptable carriers, excipients or stabilizers (*Remington's Pharmaceutical Sciences* 18th edition, Mack Publishing Co., Easton, Pa. 18042 [1990]). Acceptable carriers, excipients, or stabilizers are nontoxic to recipients at the dosages and concentrations employed, and include buffers, antioxidants including ascorbic acid, methionine, Vitamin E, sodium metabisulfite, preservatives, isotonicifiers, stabilizers, metal complexes (e.g., Zn-protein complexes), and/or chelating agents such as EDTA.

When the therapeutic agent is an antibody fragment, the smallest fragment which specifically binds to the binding domain of the target protein is preferred. For example, based upon the variable region sequences of an antibody, antibody fragments or even peptide molecules can be designed which retain the ability to bind the target protein sequence. Such peptides can be synthesized chemically and/or produced by recombinant DNA technology (see, e.g., Marasco et al., *Proc. Natl. Acad. Sci. USA* 90: 7889-7893 [1993]).

Buffers are used to control the pH in a range which optimizes the therapeutic effectiveness, especially if stability is pH dependent. Buffers are preferably present at concentrations ranging from about 50 mM to about 250 mM. Suitable buffering agents for use with the present invention include both organic and inorganic acids and salts thereof. For example, citrate, phosphate, succinate, tartrate, fumarate, gluconate, oxalate, lactate, acetate. Additionally, buffers may be comprised of histidine and trimethylamine salts such as Tris.

Preservatives are added to retard microbial growth, and are typically present in a range from 0.2%-1.0% (w/v). Suitable preservatives for use with the present invention include octadecyldimethylbenzyl ammonium chloride; hexamethonium chloride; benzalkonium halides (e.g., chloride, bromide, iodide), benzethonium chloride; thimerosal, phenol, butyl or benzyl alcohol; alkyl parabens such as methyl or propyl paraben; catechol; resorcinol; cyclohexanol, 3-pentanol, and m-cresol.

Tonicity agents, sometimes known as "stabilizers" are present to adjust or maintain the tonicity of a liquid composition. When used with large, charged biomolecules such as proteins and antibodies, they are often termed "stabilizers"

because they can interact with the charged groups of the amino acid side chains, thereby lessening the potential for inter and intra-molecular interactions. Tonicity agents can be present in any amount between 0.1% to 25% by weight, preferably 1 to 5%, taking into account the relative amounts of the other ingredients. Preferred tonicity agents include polyhydric sugar alcohols, preferably trihydric or higher sugar alcohols, such as glycerin, erythritol, arabitol, xylitol, sorbitol and mannitol.

Additional excipients include agents which can serve as one or more of the following: (1) bulking agents, (2) solubility enhancers, (3) stabilizers and (4) and agents preventing denaturation or adherence to the container wall. Such excipients include: polyhydric sugar alcohols (enumerated above); amino acids such as alanine, glycine, glutamine, asparagine, histidine, arginine, lysine, ornithine, leucine, 2-phenylalanine, glutamic acid, threonine, etc.; organic sugars or sugar alcohols such as sucrose, lactose, lactitol, trehalose, stachyose, mannose, sorbose, xylose, ribose, ribitol, myoinisitose, myoinisitol, galactose, galactitol, glycerol, cyclitols (e.g., inositol), polyethylene glycol; sulfur containing reducing agents, such as urea, glutathione, thioctic acid, sodium thioglycolate, thioglycerol, $\alpha$-monothioglycerol and sodium thio sulfate; low molecular weight proteins such as human serum albumin, bovine serum albumin, gelatin or other immunoglobulins; hydrophilic polymers such as polyvinylpyrrolidone; monosaccharides (e.g., xylose, mannose, fructose, glucose; disaccharides (e.g., lactose, maltose, sucrose); trisaccharides such as raffinose; and polysaccharides such as dextrin or dextran.

In order for the formulations to be used for in vivo administration, they must be sterile. The formulation may be rendered sterile by filtration through sterile filtration membranes. The therapeutic compositions herein generally are placed into a container having a sterile access port, for example, an intravenous solution bag or vial having a stopper pierceable by a hypodermic injection needle.

The route of administration is in accordance with known and accepted methods, such as by single or multiple bolus or infusion over a long period of time in a suitable manner, e.g., injection or infusion by subcutaneous, intravenous, intraperitoneal, intramuscular, intraarterial, intralesional or intraarticular routes, topical administration, inhalation or by sustained release or extended-release means.

The formulation herein may also contain more than one active compound as necessary for the particular indication being treated, preferably those with complementary activities that do not adversely affect each other. Alternatively, or in addition, the composition may comprise a cytotoxic agent, cytokine or growth inhibitory agent. Such molecules are suitably present in combination in amounts that are effective for the purpose intended.

The active ingredients may also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in *Remington's Pharmaceutical Sciences* 18th edition, supra.

Sustained-release preparations may be prepared. Suitable examples of sustained-release preparations include semipermeable matrices of solid hydrophobic polymers containing the antibody, which matrices are in the form of shaped articles, e.g., films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and γ-ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(−)-3-hydroxybutyric acid. Microencapsulation of recombinant proteins for sustained release has been successfully performed with human growth hormone (rhGH), interferon-(rhIFN-), interleukin-2, and MN rpg 120. Johnson et al., *Nat. Med.* 2: 795-799 (1996); Yasuda et al., *Biomed. Ther.* 27: 1221-1223 (1993); Hora et al., *Bio/Technology* 8: 755-758 (1990); Cleland, "Design and Production of Single Immunization Vaccines Using Polylactide Polyglycolide Microsphere Systems," in *Vaccine Design: The Subunit and Adjuvant Approach*, Powell and Newman, eds., (Plenum Press: New York, 1995), pp. 439-462; WO 97/03692; WO 96/40072; WO 96/07399; and U.S. Pat. No. 5,654,010.

The sustained-release formulations of these proteins may be developed using poly lactic-coglycolic acid (PLGA) polymer due to its biocompatibility and wide range of biodegradable properties. The degradation products of PLGA, lactic and glycolic acids, can be cleared quickly within the human body. Moreover, the degradability of this polymer can be adjusted from months to years depending on its molecular weight and composition. Lewis, "Controlled release of bioactive agents from lactide/glycolide polymer", in *Biodegradable Polymers as Drug Deliver*); Systems (Marcel Dekker; New York, 1990), M. Chasin and R. Langer (Eds.) pp. 1-41.

While polymers such as ethylene-vinyl acetate and lactic acid-glycolic acid enable release of molecules for over 100 days, certain hydrogels release proteins for shorter time periods. When encapsulated antibodies remain in the body for a long time, they may denature or aggregate as a result of exposure to moisture at 37° C., resulting in a loss of biological activity and possible changes in immunogenicity. Rational strategies can be devised for stabilization depending on the mechanism involved. For example, if the aggregation mechanism is discovered to be intermolecular S—S bond formation through thio-disulfide interchange, stabilization may be achieved by modifying sulfhydryl residues, lyophilizing from acidic solutions, controlling moisture content, using appropriate additives, and developing specific polymer matrix compositions.

Liposomal or proteinoid compositions may also be used to formulate the proteins or antibodies disclosed herein. See U.S. Pat. Nos. 4,925,673 and 5,013,556.

Stability of the proteins and antibodies described herein may be enhanced through the use of non-toxic "water-soluble polyvalent metal salts". Examples include $Ca^{2+}$, $Mg^{2+}$, $Zn^{2+}$, $Fe^{2+}$, $Fe^{3+}$, $Cu^{2+}$, $Sn^{2+}$, $Sn^{3+}$, $Al^{2+}$ and $Al^{3+}$. Example anions that can form water soluble salts with the above polyvalent metal cations include those formed from inorganic acids and/ or organic acids. Such water-soluble salts have a solubility in water (at 20° C.) of at least about 20 mg/ml, alternatively at least about 100 mg/ml, alternative at least about 200 mg/ml.

Suitable inorganic acids that can be used to form the "water soluble polyvalent metal salts" include hydrochloric, acetic, sulfuric, nitric, thiocyanic and phosphoric acid. Suitable organic acids that can be used include aliphatic carboxylic acid and aromatic acids. Aliphatic acids within this definition may be defined as saturated or unsaturated $C_{2-9}$ carboxylic acids (e.g., aliphatic mono-, di- and tri-carboxylic acids). For example, exemplary monocarboxylic acids within this definition include the saturated $C_{2-9}$ monocarboxylic acids acetic, proprionic, butyric, valeric, caproic, enanthic, caprylic pelargonic and capryonic, and the unsaturated $C_{2-9}$ monocarboxylic acids acrylic, propriolic methacrylic, crotonic and isocrotonic acids. Exemplary dicarboxylic acids include the saturated $C_{2-9}$ dicarboxylic acids malonic, succinic, glutaric, adipic and pimelic, while unsaturated $C_{2-9}$ dicarboxylic acids include maleic, fumaric, citraconic and mesaconic acids. Exemplary tricarboxylic acids include the saturated $C_{2-9}$ tricarboxylic acids tricarballylic and 1,2,3-butanetricarboxylic acid. Additionally, the carboxylic acids of this definition may also contain one or two hydroxyl groups to form hydroxy carboxylic acids. Exemplary hydroxy carboxylic acids include glycolic, lactic, glyceric, tartronic, malic, tartaric and citric acid. Aromatic acids within this definition include benzoic and salicylic acid.

Commonly employed water soluble polyvalent metal salts which may be used to help stabilize the encapsulated polypeptides of this invention include, for example: (1) the inorganic acid metal salts of halides (e.g., zinc chloride, calcium chloride), sulfates, nitrates, phosphates and thiocyanates; (2) the aliphatic carboxylic acid metal salts (e.g., calcium acetate, zinc acetate, calcium proprionate, zinc glycolate, calcium lactate, zinc lactate and zinc tartrate); and (3) the aromatic carboxylic acid metal salts of benzoates (e.g., zinc benzoate) and salicylates.

For the prevention or treatment of disease, the appropriate dosage of an active agent will depend on the type of disease to be treated, as defined above, the severity and course of the disease, whether the agent is administered for preventive or therapeutic purposes, previous therapy, the patient's clinical history and response to the agent, and the discretion of the attending physician. The agent is suitably administered to the patient at one time or over a series of treatments.

The method of the invention can be combined with known methods of treatment for a disorder, either as combined or additional treatments steps or as additional components of a therapeutic formulation.

Dosages and desired drug concentration of pharmaceutical compositions of the present invention may vary depending on the particular use envisioned. The determination of the appropriate dosage or route of administration is well within the skill of an ordinary artisan. Animal experiments provide reliable guidance for the determination of effective doses for human therapy. Interspecies scaling of effective doses can be performed following the principles laid down by Mordenti, J. and Chappell, W. "The Use of Interspecies Scaling in Toxicokinetics," In *Toxicokinetics and New Drug Development*, Yacobi et al., Eds, Pergamon Press, New York 1989, pp. 42-46.

When in vivo administration of the polypeptides or antibodies described herein are used, normal dosage amounts may vary from about 10 ng/kg up to about 100 mg/kg of mammal body weight or more per day, preferably about 1 mg/kg/day to 10 mg/kg/day, depending upon the route of administration. Guidance as to particular dosages and methods of delivery is provided in the literature; see, for example, U.S. Pat. No. 4,657,760; 5,206,344; or 5,225,212. It is within the scope of the invention that different formulations will be effective for different treatments and different disorders, and that administration intended to treat a specific organ or tissue may necessitate delivery in a manner different from that to another organ or tissue. Moreover, dosages may be administered by one or more separate administrations, or by continuous infusion. For repeated administrations over several days or longer, depending on the condition, the treatment is sustained until a desired suppression of disease symptoms occurs. However, other dosage regimens may be useful. The progress of this therapy is easily monitored by conventional techniques and assays.

The formulations of the present invention, including but not limited to reconstituted formulations, are administered to a mammal in need of treatment with the protein, preferably a human, in accord with known methods, such as intravenous administration as a bolus or by continuous infusion over a period of time, by intramuscular, intraperitoneal, intracerebrospinal, subcutaneous, intra-articular, intrasynovial, intrathecal, oral, topical, or inhalation routes.

In preferred embodiments, the formulations are administered to the mammal by subcutaneous (i.e., beneath the skin) administration. For such purposes, the formulation may be injected using a syringe. However, other devices for administration of the formulation are available such as injection devices (e.g., the Inject-ease™ and Genject™ devices); injector pens (such as the GenPen™); auto-injector devices, needleless devices (e.g., MediJector™ and BioJector™); and subcutaneous patch delivery systems.

In a specific embodiment, the present invention is directed to kits for a single dose-administration unit. Such kits comprise a container of an aqueous formulation of therapeutic protein or antibody, including both single or multi-chambered pre-filled syringes. Exemplary pre-filled syringes are available from Vetter GmbH, Ravensburg, Germany.

The appropriate dosage ("therapeutically effective amount") of the protein will depend, for example, on the condition to be treated, the severity and course of the condition, whether the protein is administered for preventive or therapeutic purposes, previous therapy, the patient's clinical history and response to the protein, the type of protein used, and the discretion of the attending physician. The protein is suitably administered to the patient at one time or over a series of treatments and may be administered to the patient at any time from diagnosis onwards. The protein may be administered as the sole treatment or in conjunction with other drugs or therapies useful in treating the condition in question.

Where the protein of choice is an antibody, from about 0.1-20 mg/kg is an initial candidate dosage for administration to the patient, whether, for example, by one or more separate administrations. However, other dosage regimens may be useful. The progress of this therapy is easily monitored by conventional techniques.

In another embodiment of the invention, an article of manufacture is provided which contains the formulation and preferably provides instructions for its use. The article of manufacture comprises a container. Suitable containers include, for example, bottles, vials (e.g., dual chamber vials), syringes (such as single or dual chamber syringes) and test tubes. The container may be formed from a variety of materials such as glass or plastic. The label, which is on, or associated with, the container holding the formulation may indicate directions for reconstitution and/or use. The label may further indicate that the formulation is useful or intended for subcutaneous administration. The container holding the formulation may be a multi-use vial, which allows for repeat administrations (e.g., from 2-6 administrations) of the reconstituted formulation. The article of manufacture may further comprise a second container comprising a suitable diluent (e.g., BWFI). Upon mixing of the diluent and the lyophilized formulation, the final protein concentration in the reconstituted formulation will generally be at least 50 mg/ml. The article of manufacture may further include other materials desirable from a commercial and user standpoint, including other buffers, diluents, filters, needles, syringes, and package inserts with instructions for use.

The invention will be more fully understood by reference to the following examples. They should not, however, be construed as limiting the scope of the invention. All citations throughout the disclosure are hereby expressly incorporated by reference.

Example 1

Investigation of Alkylglycosides as Nonionic Surfactants to Prevent Aggregation of Proteins/Antibodies This example illustrates use of alkylglycosides as non-ionic surfactants to prevent aggregation of antibodies in aqueous solution. The protective action of various alkylglycosides and polysorbate 20 against agitation-induced aggregation of various monoclonal antibodies in solution was evaluated in using two different forms of agitation: shaking and stirring.

Shaking-Induced Aggregation

In this set of studies, a buffered solution (20 mM sodium phosphate buffer, pH 7.4) of monoclonal antibody was subjected to shaking on an orbital shaker at 150 rpm, at a controlled temperature of 37° C. These studies were carried out using a 3 ml solution fill of the antibody solution in a 6 cc glass vial. Samples were withdrawn at regular intervals and analyzed for percent monomer using size-exclusion chromatography. Various surfactants of the class of alkylglycosides were evaluated for their effectiveness to prevent protein aggregation during shaking. The surfactants were used at concentrations below their respective critical micelle concentration (CMC) or above their respective CMC.

Stirring-Induced Aggregation

In this set of studies, a Tefloncoated magnetic stir bar was used to induce agitation in a buffered solution (20 mM histidine-acetate, pH 5.5) of monoclonal antibody. 3 ml of the antibody solution was filled in a 6 cc glass vial and the solution was stirred at 500 rpm using a Teflon-coated stir bar. The solution was stirred for a period of 90 minutes and samples were withdrawn at regular intervals and analyzed for turbidity as an indication of formation of insoluble aggregates. Various surfactants of the class of alkylglycosides were evaluated for their effectiveness to prevent protein aggregation during shaking. The surfactants were used at concentrations below their respective critical micelle concentration (CMC) or above their respective CMC.

Results

FIG. 1 shows the time-dependence of the percent monomer of an anti-MUC16 monoclonal antibody in solution, following shaking at 150 rpm at 37° C. for 64 hours containing no surfactant, and in the presence of various surfactants including n-decyl-β-D-glucopyranoside, n-octyl-β-D-glucopyranoside or polysorbate 20. The surfactants were employed at one half the concentration of their respective CMC values, i.e., 1.1 mM (0.035% w/v) n-decyl-β-D-glucopyranoside, 9 mM (0.24%) n-octyl-β-D-glucopyranoside and 0.04 mM (0.0035%) polysorbate 20.

As shown in FIG. 1, in the absence of any surfactant, a decrease in the percent monomer of the antibody was observed upon shaking over a period of 64 hours. While polysorbate 20 was not effective in preventing shaking-induced loss of monomer under these conditions, the two surfactants of the class of alkylglycosides tested, i.e., n-decyl-β-D-glucopyranoside and n-octyl-β-D-glucopyranoside, were effective in preventing loss of monomer of the anti-MUC16 monoclonal antibody upon shaking Hence, both n-decyl-β-D-glucopyranoside and n-octyl-β-D-glucopyranoside (i.e., alkylglycosides having CMC values of greater than 1.0 mM) effectively prevent agitation-induced aggregation of the anti-MUC16 monoclonal antibody in solution.

Figure 2:
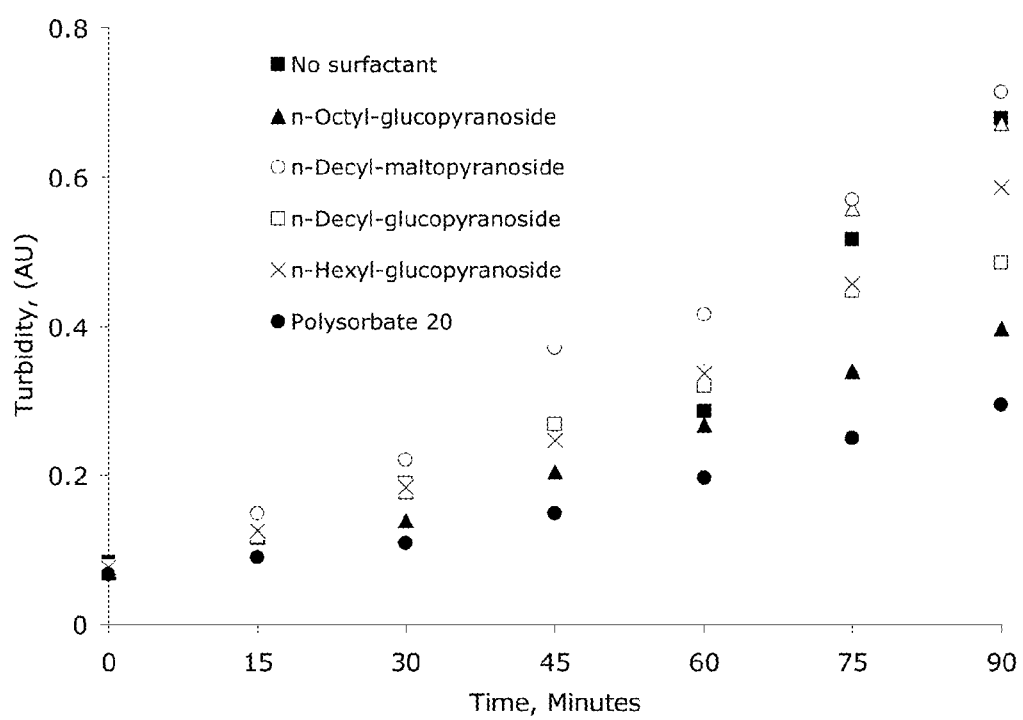
FIG. 2 shows the effect of certain surfactants on agitation-induced aggregation of an anti-MUC16 monoclonal antibody in aqueous solution.
Figure 3:
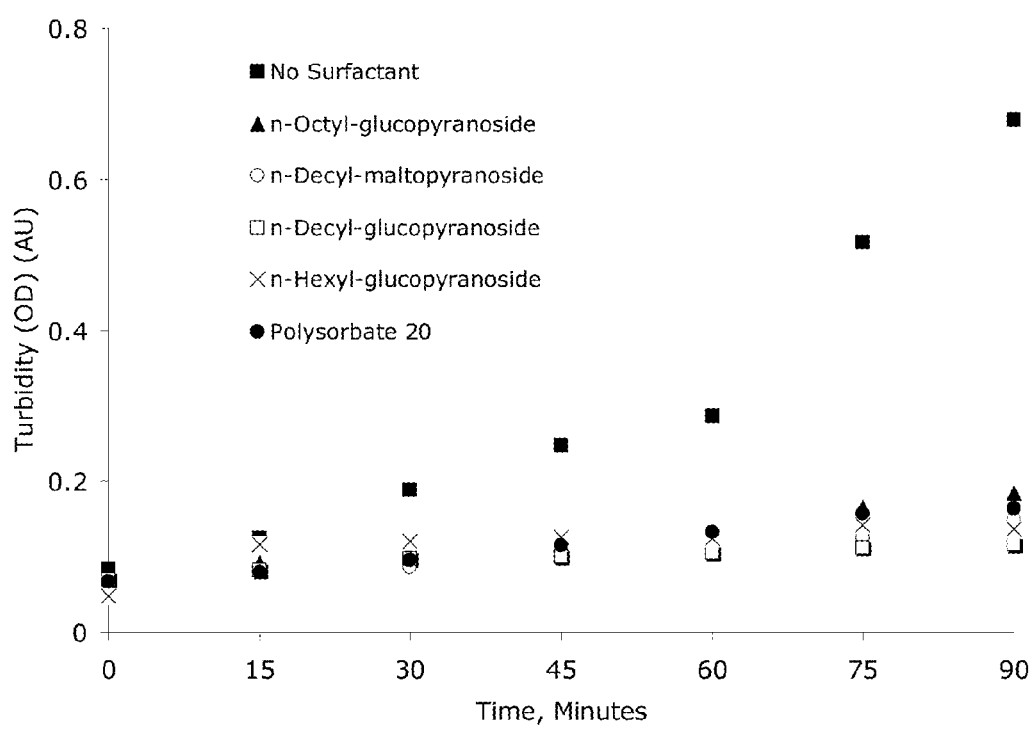
FIG. 3 shows the effect of certain surfactants on agitation-induced aggregation of an anti-MUC16 monoclonal antibody in aqueous solution.

FIGS. 2 and 3 show the time-course of turbidity formation in a solution of the anti-MUC16 monoclonal antibody following stirring at 500 rpm using a Teflon-coated magnetic bar at ambient temperature for a period of 90 minutes. Turbidity was evaluated in solutions containing no surfactant as well as in solutions containing different alkylglycoside surfactants or polysorbate 20. In FIG. 2, the surfactant concentration employed was one-tenth of their respective CMC values, i.e., 1.8 mM (0.053%) n-octyl-β-D-glucopyranoside, 0.18 mM (0.008%) n-decyl-β-D-maltopyranoside, 0.22 mM (0.007%) n-decyl-β-D-glucopyranoside, 25 mM (0.66%) n-hexyl-β-D-glucopyranoside and 0.008 mM (0.0007%) polysorbate 20. In FIG. 3, the surfactant concentration employed was twice their respective CMC values, i.e., 36 mM (1.0%) n-octyl-β-D-glucopyranoside, 3.6 mM (0.16%) n-decyl-β-D-maltopyranoside, 4.4 mM (0.14%) n-decyl-β-D-glucopyranoside, 500 mM (12%) n-hexyl-β-D-glucopyranoside and 0.16 mM (0.014%) polysorbate 20.

As seen in FIG. 2, at one-tenth the concentration of their respective CMC values, n-octyl-β-D-glucopyranoside and polysorbate 20 were effective in preventing turbidity development compared to the antibody solution containing no surfactant. The formation of turbidity is typically attributed to formation of large insoluble aggregates of the antibody.

As further seen in FIG. 3, at twice the concentration of their respective CMCs, all surfactants of the class of alkylglycosides were effective in preventing aggregation of the antibody in solution as measured by turbidity formation.

Figure 4:
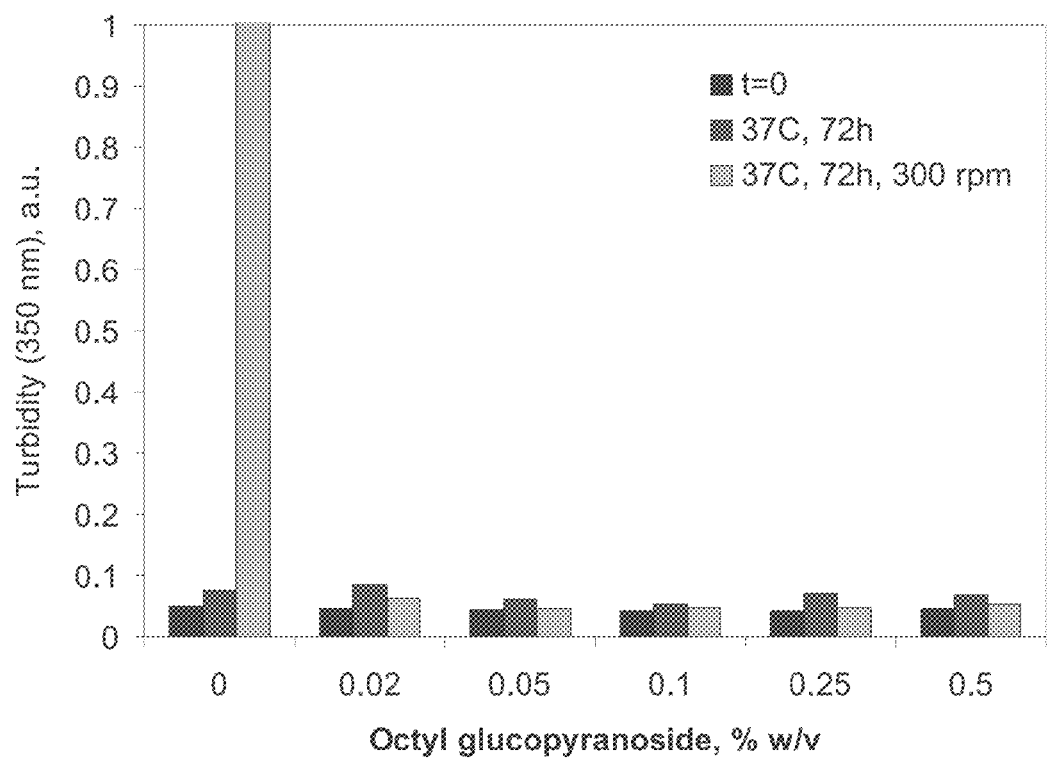
FIG. 4 shows the effect of n-octyl-β-D-glucopyranoside on the turbidity of aqueous solutions comprising an anti-MUC16 monoclonal antibody.

In FIG. 4, the effect of varying the concentration of n-octyl-β-D-glucopyranoside on the turbidity of anti-MUC16 monoclonal antibody formulations during shaking at 300 rpm for 72 hours at 37° C. was investigated. As shown in FIG. 4, at all the various concentrations tested, i.e., 0.72 mM (0.02 w/v), 1.8 mM (0.05 w/v), 3.6 mM (0.1 w/v), 9 mM (0.25 w/v), 18 mM (0.5 w/v), n-octyl-β-D-glucopyranoside effectively inhibited the formation of visible antibody aggregates upon shaking as measured by turbidity formation.

Figure 5:
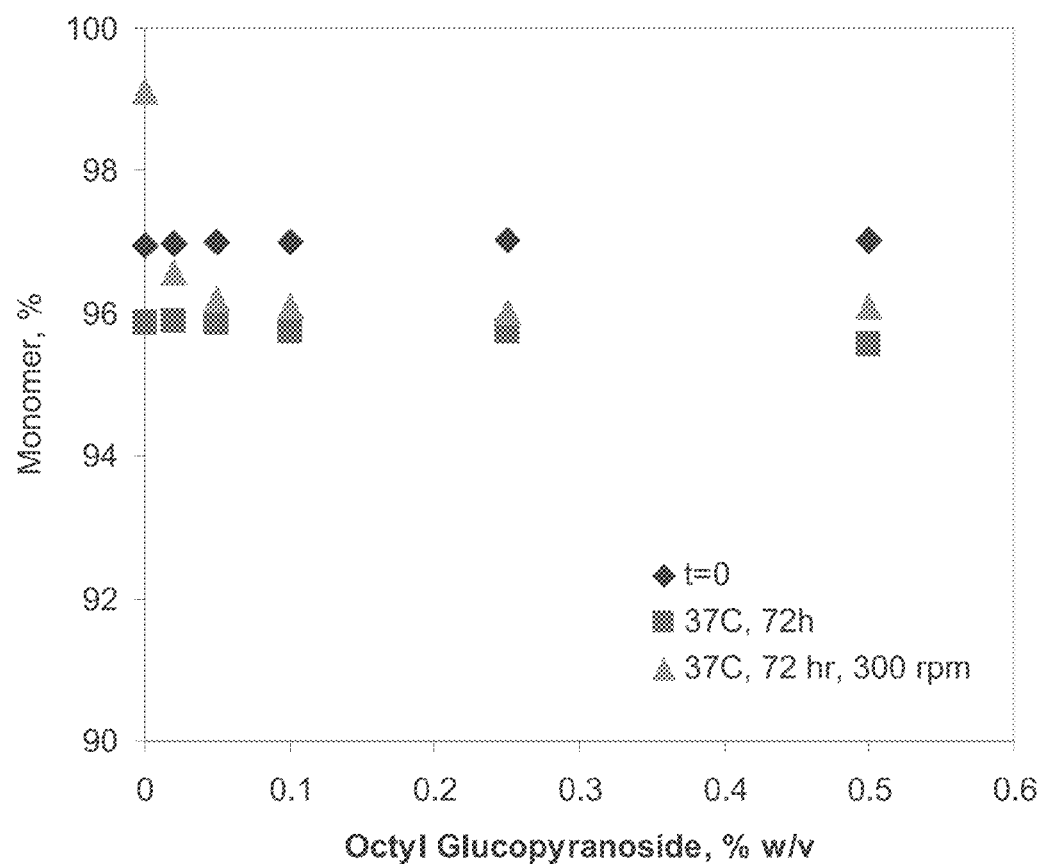
FIG. 5 shows the effect of n-octyl-β-D-glucopyranoside on the maintenance of % monomer of an anti-MUC16 monoclonal antibody in aqueous solution.
Figure 6:
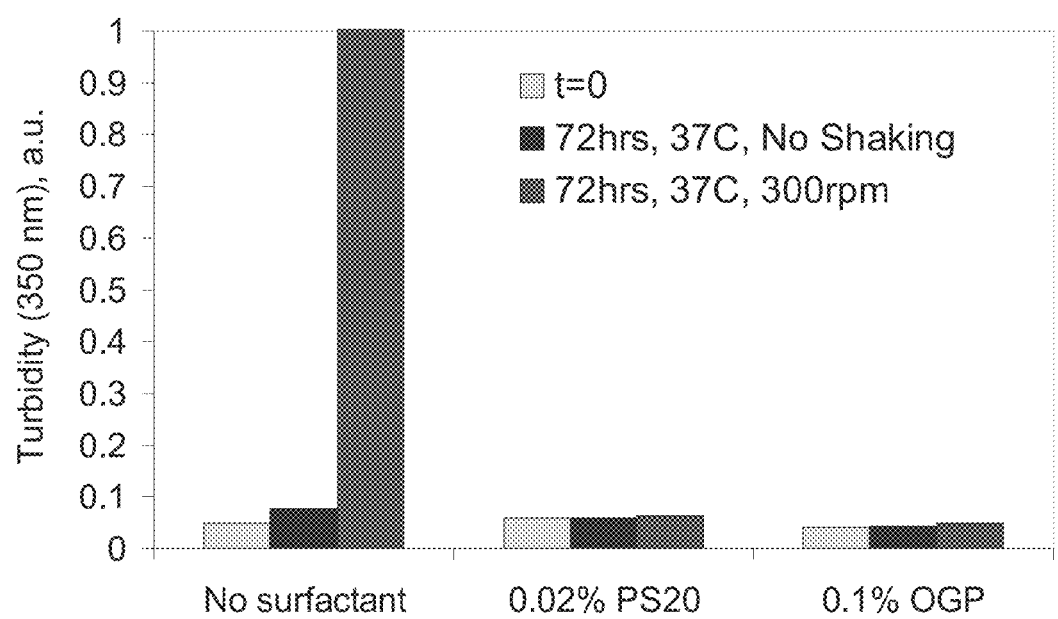
FIG. 6 shows the effect of n-octyl-β-D-glucopyranoside or polysorbate 20 on the turbidity of aqueous solutions comprising an anti-MUC16 monoclonal antibody.
Figure 7:
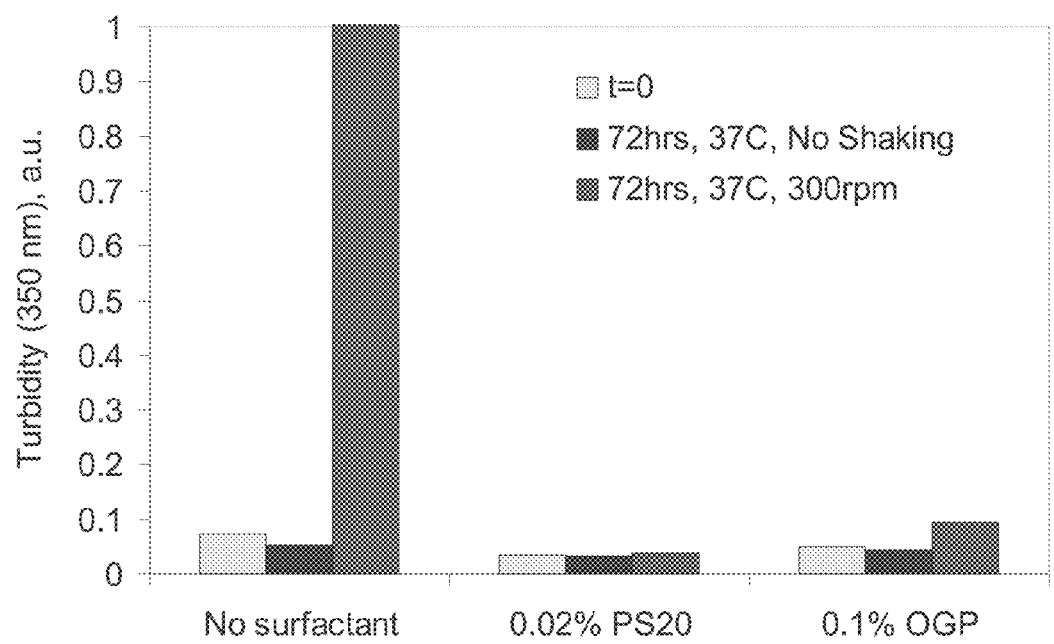
FIG. 7 shows the effect of n-octyl-β-D-glucopyranoside or polysorbate 20 on the turbidity of aqueous solutions comprising an anti-IgE monoclonal antibody.
Figure 8:
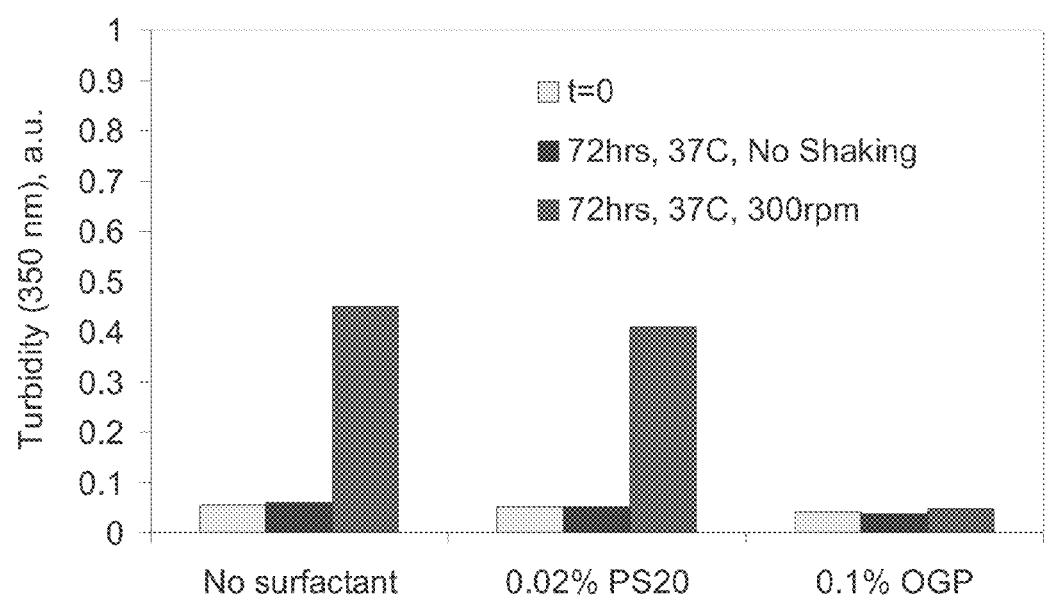
FIG. 8 shows the effect of n-octyl-β-D-glucopyranoside or polysorbate 20 on the turbidity of aqueous solutions comprising an anti-CD11a monoclonal antibody.
Figure 9:
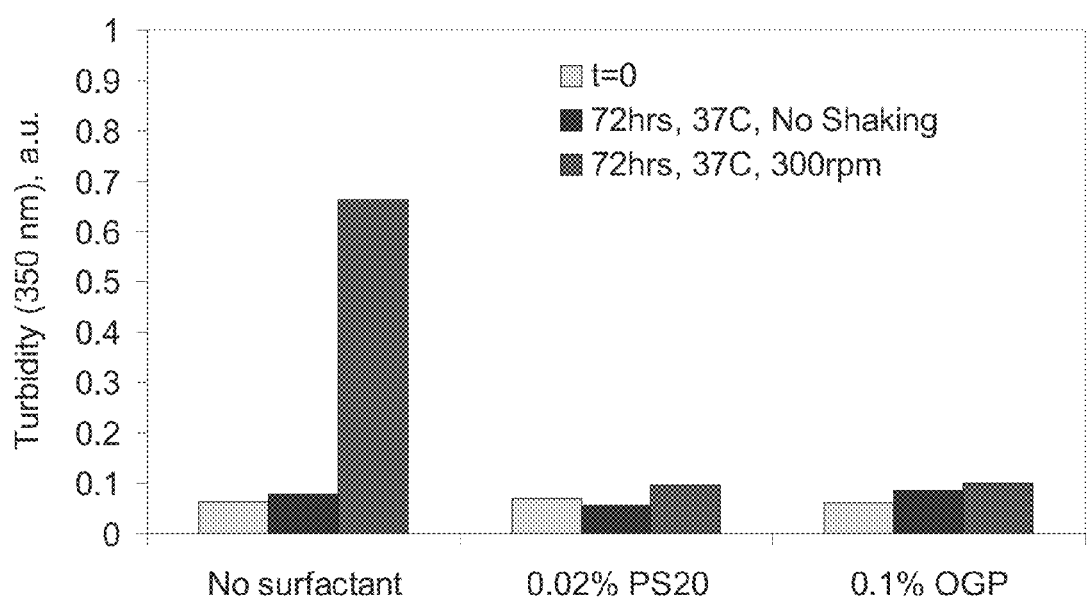
FIG. 9 shows the effect of n-octyl-β-D-glucopyranoside or polysorbate 20 on the turbidity of aqueous solutions comprising an anti-CD22 monoclonal antibody.
Figure 10:
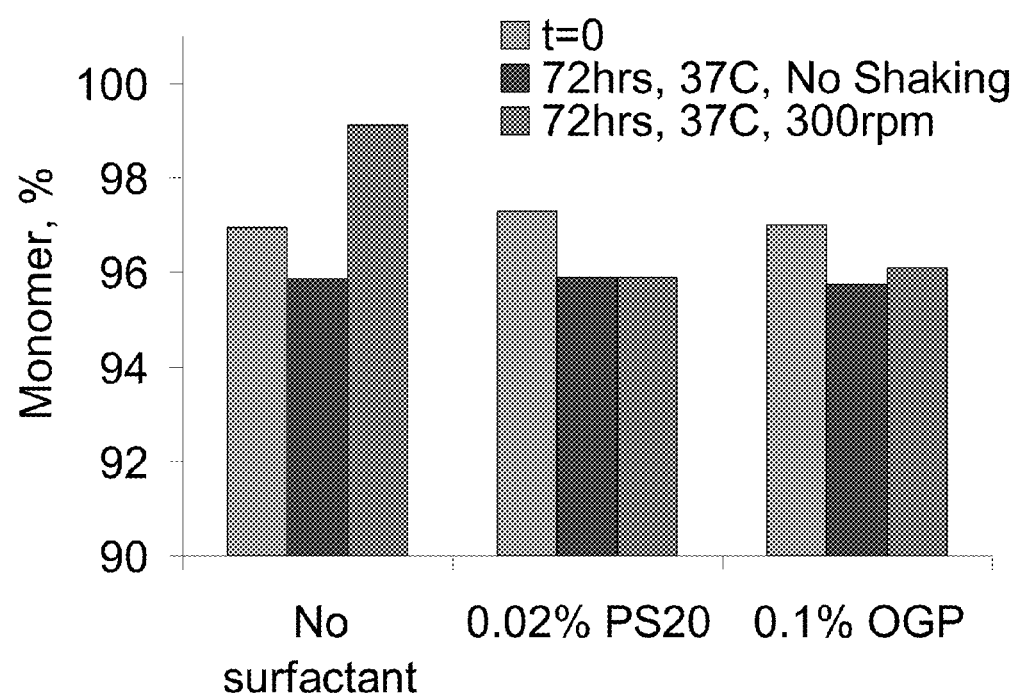
FIG. 10 shows the effect of n-octyl-β-D-glucopyranoside or polysorbate 20 on the maintenance of % monomer of an anti-MUC16 monoclonal antibody in aqueous solution.
Figure 11:
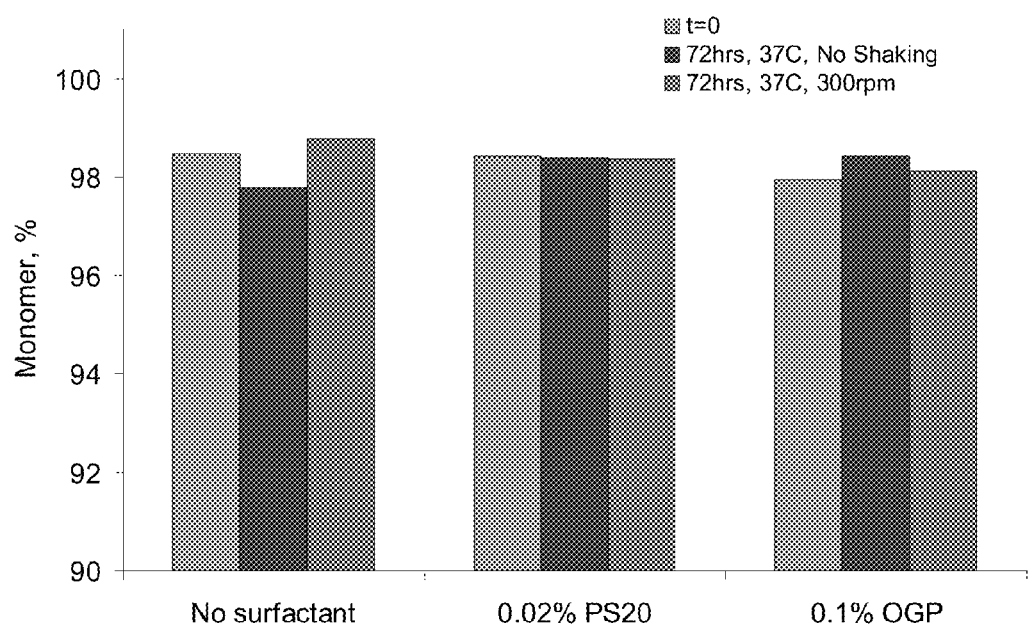
FIG. 11 shows the effect of n-octyl-β-D-glucopyranoside or polysorbate 20 on the maintenance of % monomer of an anti-IgE monoclonal antibody in aqueous solution.
Figure 12:
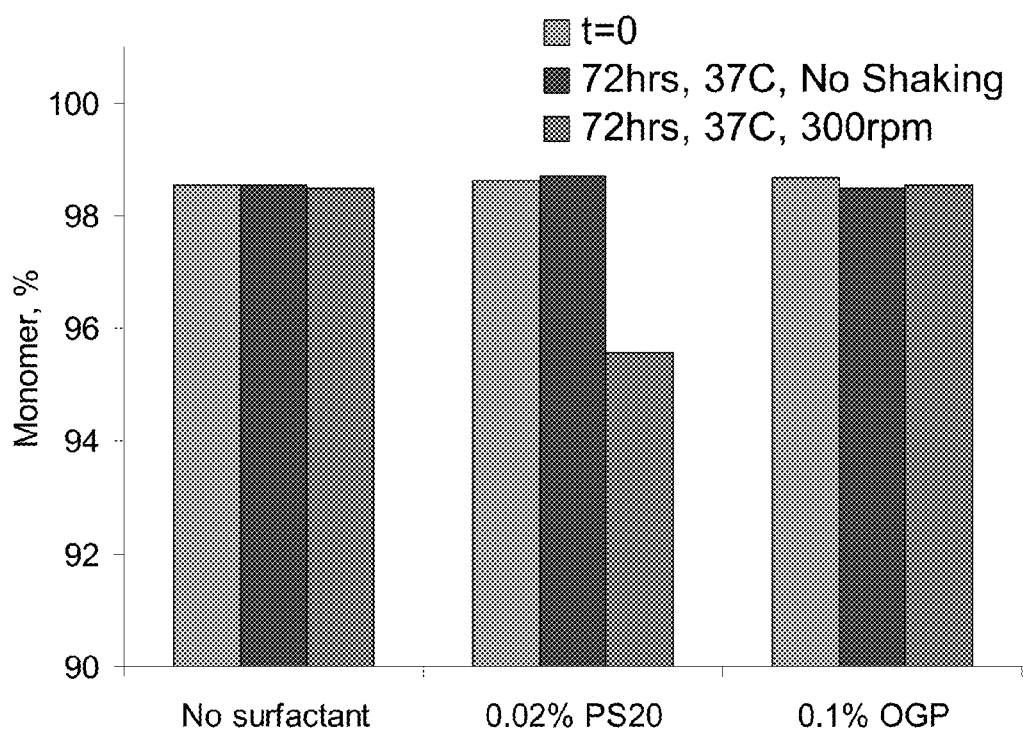
FIG. 12 shows the effect of n-octyl-β-D-glucopyranoside or polysorbate 20 on the maintenance of % monomer of an anti-CD11a monoclonal antibody in aqueous solution.
Figure 13:
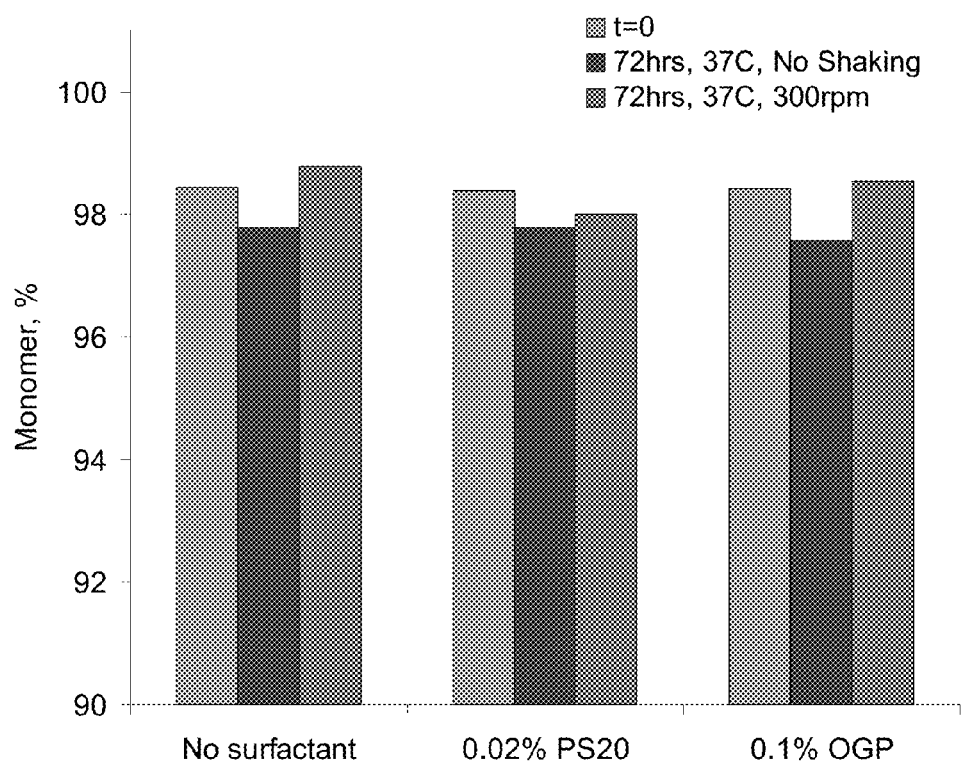
FIG. 13 shows the effect of n-octyl-β-D-glucopyranoside or polysorbate 20 on the maintenance of % monomer of an anti-CD22 monoclonal antibody in aqueous solution.

In FIG. 5, the effect of varying the concentration of n-octyl-β-D-glucopyranoside on the percent monomer of the anti-MUC16 monoclonal antibody in solution, following shaking at 300 rpm at 37° C. for 72 hours was investigated. As shown in FIG. 5, at all the various concentrations tested, n-octyl-β-D-glucopyranoside effectively maintained the percent monomer of the anti-MUC16 antibody upon shaking as compared to that of an unshaken sample stored under similar conditions.

In FIGS. 6-9, the effect of 0.23 mM (0.02% w/v) polysorbate 20 or 3.6 mM (0.1% w/v) n-octyl-β-D-glucopyranoside on the turbidity of aqueous formulations of an anti-MUC16 monoclonal antibody (FIG. 6), an anti-IgE monoclonal antibody (FIG. 7), an anti-CD11a monoclonal antibody (FIG. 8), and an anti-CD22 monoclonal antibody (FIG. 9), during shaking at 300 rpm for 72 hours at 37° C. was investigated. As shown in FIGS. 6-9, both polysorbate 20 and n-octyl-β-D-glucopyranoside effectively inhibited the formation of visible antibody aggregates for all antibodies tested upon shaking as measured by turbidity formation.

In FIGS. 10-13, the effect of 0.23 mM (0.02% w/v) polysorbate 20 or 3.6 mM (0.1% w/v) n-octyl-β-D-glucopyranoside on the percent monomer of aqueous formulations of an anti-MUC16 monoclonal antibody (FIG. 10), an anti-IgE monoclonal antibody (FIG. 11), an anti-CD11a monoclonal antibody (FIG. 12), and an anti-CD22 monoclonal antibody (FIG. 13), during shaking at 300 rpm for 72 hours at 37° C. was investigated. As shown in FIGS. 10-13, n-octyl-β-D-glucopyranoside effectively maintained the percent monomer of the various antibodies tested upon shaking as compared to that of an unshaken sample stored under similar conditions.

Example 2

Investigation of Alkylglycosides as Nonionic Surfactants to Prevent Oxidation of Proteins/Antibodies This example illustrates use of alkylglycosides as non-ionic surfactants to prevent against the oxidation of antibodies in aqueous solution.

In a first experiment, solutions of surfactants of the class of alkylglycosides, i.e., n-decyl-β-D-glucopyranoside, n-octyl-β-D-glucopyranoside, and n-decyl-β-D-maltopyranoside, as well as polysorbate 20 at a concentration of 0.1% w/v in water were stored at 40° C. for a period of one month. Samples were then withdrawn and analyzed for the presence of hydrogen peroxide using the Amplex Red Hydrogen Peroxide assay. the results of these analyses are shown in FIG. 14.

Figure 14:
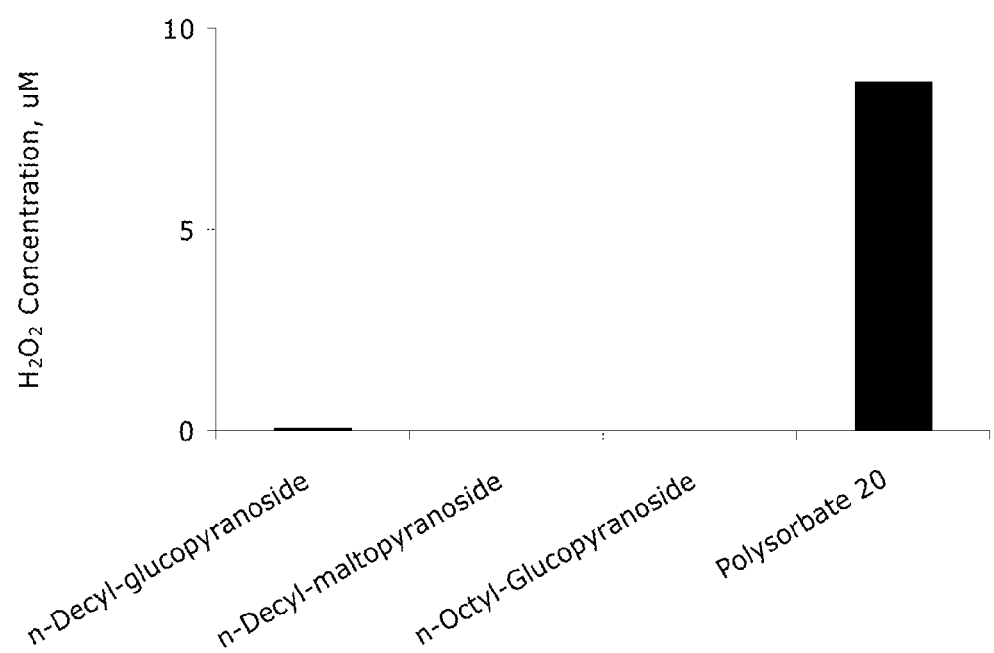
FIG. 14 shows the amount of hydrogen peroxide generated by various alkylglycosides or polysorbate 20 in solution over time.

As shown in FIG. 14, alkylglycoside surfactant-containing solutions produce negligible amounts of hydrogen peroxide following storage of these solutions at 40° C. for a period of one month. In contrast, about 10 μM of hydrogen peroxide was formed in the polysorbate 20 containing solution under similar storage conditions. These data suggest that the use of alkylglycosides as protein stabilizing agents in aqueous formulations may be preferable as compared to polysorbate 20, because of the relatively lower propensity of alkylglycosides to produce oxidating hydrogen peroxide over time in solution.

In a second experiment, oxidation of the Met256 amino acid residue in an anti-CD11a monoclonal antibody in solutions containing either n-decyl-β-D-glucopyranoside, n-octyl-β-D-glucopyranoside, or polysorbate 20 was evaluated. For this purpose, 3 ml of the buffered antibody solution (pH 6.0) containing 0.1% w/v of the surfactant was stored in 6 cc vials at either 5° C. or 40° C. for a period of either 2 or 4 weeks. Samples were then withdrawn and analyzed for oxidation of the Met256 residue, an amino acid in anti-CD11a primary amino acid sequence that has previously been shown to be prone to oxidation. the results of these analyses are shown in FIG. 15.

Figure 15:
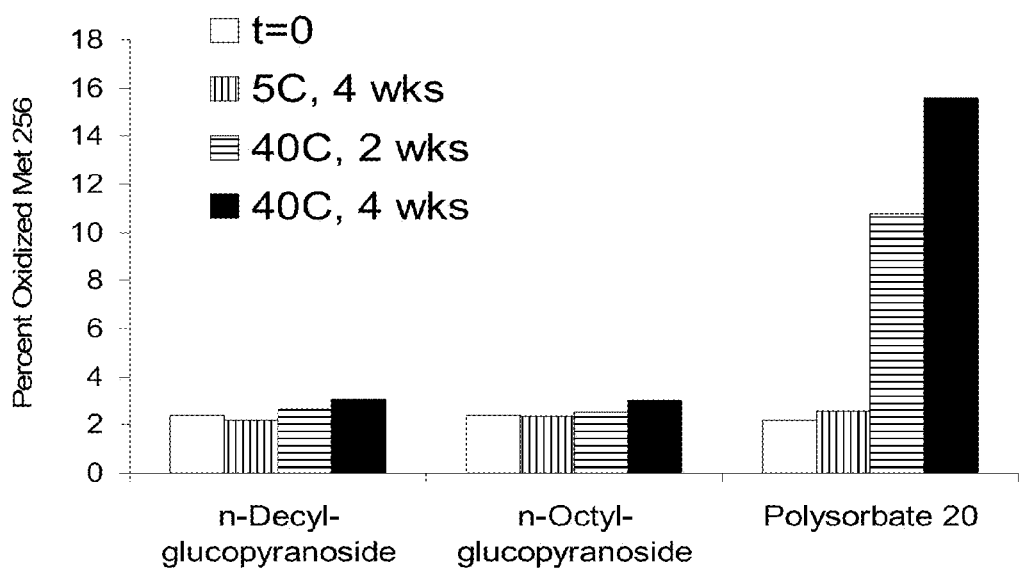
FIG. 15 shows the effect of various alkylglycosides or polysorbate 20 on the prevention of oxidation of an anti-CD11a antibody in aqueous solution.

As shown in FIG. 15, no significant increase in the percent oxidized Met256 of anti-CD11a was observed in solutions containing n-decyl-β-D-glucopyranoside or n-octyl-β-D-glucopyranoside following storage as described above, as compared to the initial sample. In polysorbate 20-containing anti-CD11a solutions, however, approximately 16% of the Met256 residues were found to be oxidized following storage at 40° C. for a period of 4 weeks, compared to a approximately 2% oxidation of the same amino acid residue at time zero. Thus, these data suggest that the use of alkylglycosides as protein stabilizing agents in aqueous formulations may be preferable as compared to polysorbate 20, because of the relatively lower propensity of alkylglycosides to oxidize the formulated protein over time in solution.

In a third experiment, Fenton reagent-induced oxidation of Met and Trp amino acid residues (i.e., amino acids known to be susceptible to oxidation) in an anti-CD22 monoclonal antibody was analyzed. Specifically, buffered (20 mM histidine acetate, pH 5.5) solutions of anti-CD22 monoclonal antibody containing 0.1 ppm $Fe^{3+}$ and 1 ppm hydrogen peroxide were prepared and stored for either 2 or 4 weeks at 40° C., either in the absence of surfactant or in the presence of 0.23 mM (0.02% w/v) polysorbate 20 or 3.6 mM (0.1% w/v) n-octyl-β-D-glucopyranoside. samples were then withdrawn and percent oxidation of Met and Trp residues was determined from the percent early peaks of the antibody eluting through a phenyl RP-HPLC column. The results from these analyses are shown in FIG. 16.

Figure 16:
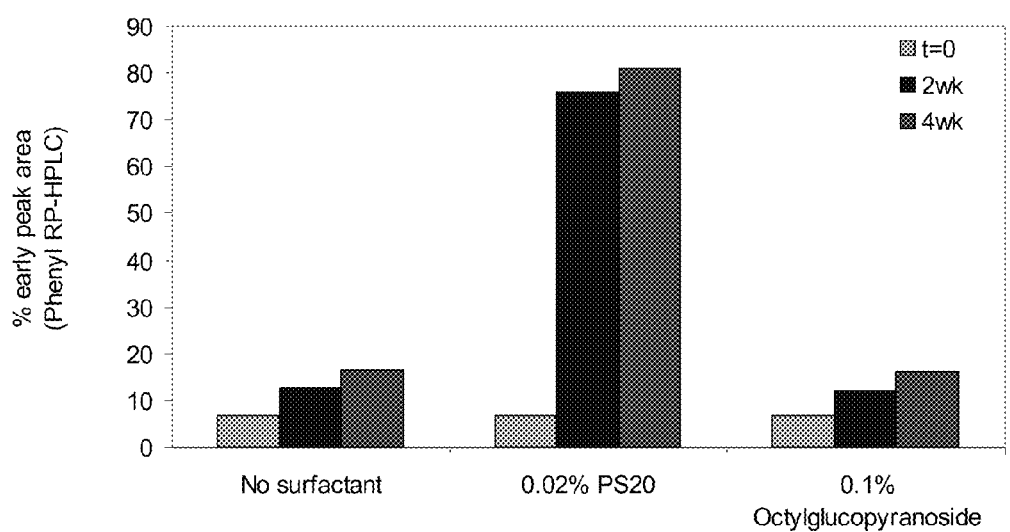
FIG. 16 shows the effect of various alkylglycosides or polysorbate 20 on the prevention of oxidation of an anti-CD22 antibody in aqueous solution.

As shown in FIG. 16, Fenton reagent-induced oxidation of susceptible amino acids (Tip, Met) in the monoclonal anti-CD22 is inhibited in solutions containing n-octyl-β-D-glucopyranoside as compared to those containing polysorbate 20, and is comparable to solutions containing no surfactant. Thus, these data suggest that the use of alkylglycosides as protein stabilizing agents in aqueous formulations may be preferable as compared to polysorbate 20, because of the relatively lower propensity of alkylglycosides to oxidize the formulated protein over time in solution.

Example 3

Investigation of Alkylglycosides as Nonionic Surfactants to Prevent Light-Induced Oxidation of Tryptophan Residues in Proteins/Antibodies This example illustrates use of alkylglycosides as non-ionic surfactants to prevent light-induced oxidation of tryptophan residues on protein/antibodies in aqueous solution.

All the following experiment were conducted as follows.

MAb Samples and Light Treatment:

Humanized anti-oxidized LDL monoclonal antibody, was produced at Genentech, Inc. from a CHO cell line. Three independent samples were prepared for photostability studies: 1) control sample, vial wrapped with aluminum foil; 2) test sample, vial light exposed (unwrapped); 3) test sample, vial light exposed (unwrapped) containing the specified nonionic surfactant. Both control & light exposed samples were kept in a light box for 24 hrs. Light exposure following ICH guideline with following setting for a Atlas SUNTEST CPS+ Light Box: Irradiance level=250 watts/square meter; Time set for 24 hours; Total UV dose=538 watt-hours/square meter; Total visible dose=1,320,000 lux-hours.

LC/MS/MS of Tryptic MAb Peptide Map:

Samples were digested with trypsin after reduction and alkylation. The resulting peptides were analyzed with a Thermo LTQ-Orbitrap mass spectrometer coupled with an Agilent 1200 capillary HPLC system. HPLC column: Jupiter Sum C18 250×1.0 mm, flow rate: 70 uL/min, column oven temperature: 55° C. Solvent A: 0.1% TFA in water, B: 0.09% TFA in 90% ACN. Orbitrap setting: MS resolution 60000, MS/MS collected in data dependent mode, using LTQ.

Fluorescence Measurements:

Intrinsic tryptophan fluo-rescence emission spectra of solutions were obtained using a Horiba Jobin Yvon Fluoromax-4 Spectrofluorometer (Edison, N.J.) equipped with a temperature-controlled water bath. A tryptophan emission spectrum was collected from 300 to 450 nm upon excitation at 295 nm.

The effect of light, and the protective effect of non-ionic surfactants, on the oxidation of tryptophan residues on an anti-oxidized LDL antibody was determined. The antibody tested possesses tryptophan residues at amino acid positions 33 (i.e., Trp33) and 92 (i.e., Trp92) and the percent light-induced oxidation at those sites was determined as described above. the results of these analyses are shown in Table 2 below.

TABLE 2

| Conditions/Surfactant | % Oxidized Trp33 | % Oxidized Trp92 |
| --- | --- | --- |
| No Light/No Surfactant | 0.0% | 0.6% |
| Light/No Surfactant | 0.3% | 6.0% |
| Light/0.39 mM n-hexyl-β-D-glucopyranoside | 0.3% | 4.9% |
| Light/300 mM n-hexyl-β-D-glucopyranoside | 0.0% | 1.6% |
| Light/0.39 mM n-hexyl-β-D-maltopyranoside | 0.3% | 5.7% |
| Light/300 mM n-hexyl-β-D-maltopyranoside | 0.0% | 2.2% |
| Light/0.03 mM n-dodecyl-β-D-maltopyranoside | 0.0% | 10.6% |
| Light/0.39 mM n-dodecyl-β-D-maltopyranoside | 0.1% | 2.7% |
| Light/0.03 mM n-dodecyl-β-D-glucopyranoside | 0.4% | 8.9% |
| Light/0.02% polysorbate 20 | 0.6% | 8.9% |

CONCLUSIONS

Alkylglycosides having CMC values of about 1 mM or greater confer stability against agitation-induced aggregation of proteins, including monoclonal antibodies.

The stability against agitation-induced aggregation conferred by alkylglycosides having CMC values of about 1 mM or greater is not antibody dependent in that the beneficial effect is observed with various antibodies of different amino acid sequence.

Surprisingly, the stability against agitation-induced aggregation conferred by alkylglycosides having CMC values of about 1 mM or greater is observed when the alkylglycoside is employed at a concentration that is below its respective CMC value.

Unlike polysorbate 20, alkylglycosides having CMC values of about 1 mM or higher did not form hydrogen peroxide upon storage for a prolonged duration of time.

Unlike polysorbate 20, alkylglycosides having CMC values of about 1 mM or greater do not significantly induce oxidation of oxidation-susceptible amino acids in various monoclonal antibodies.

Unlike polysorbate 20, alkylglycosides having CMC values of about 1 mM or greater are capable of inhibiting or reducing the amount of light-induced oxidation of tryptophan residues in antibodies and other proteins, particularly when used at a concentration which is above their respective CMC value.

What is claimed is:

1. A method of inhibiting agitation-induced aggregation of an antibody present in a first aqueous solution, said method comprising the step of adding to said first aqueous solution an agitation-induced aggregation inhibiting amount of an alkylglycoside having a CMC value of about 1.0 mM or greater in water at 25° C., wherein the alkylglycoside is added to a final concentration that is lower than the CMC value of the alkylglycoside in water at 25° C., thereby providing a second aqueous solution.

2. The method of claim 1, wherein the antibody is a monoclonal antibody.

3. The method of claim 1, wherein the alkylglycoside is selected from the group consisting of n-hexyl-β-D-glucopyranoside, n-heptyl-β-D-glucopyranoside, n-octyl-β-D-glucopyranoside, n-nonyl-β-D-glucopyranoside, n-decyl-β-D-glucopyranoside, 3-cyclohexyl-1-propyl-β-D-glucoside, 3-cyclohexyl-1-butyl-β-D-glucoside, n-hexyl-β-D-maltopyranoside, n-octyl-β-D-maltopyranoside, n-nonyl-β-D-maltopyranoside, n-decyl-β-D-maltopyranoside, cyclohexyl-methyl-β-D-maltoside, 2-cyclohexyl-ethyl-β-D-maltoside, 3-cyclohexyl-propyl-β-D-maltoside, 4-cyclohexyl-butyl-β-D-maltoside, and 5-cyclohexyl-pentyl-β-D-maltoside.

4. The method of claim 1, wherein the alkylglycoside is n-octyl-β-D-glucopyranoside.

5. The method of claim 1, wherein the alkylglycoside is n-decyl-β-D-glucopyranoside.

6. The method of claim 1, wherein the alkylglycoside is n-decyl-β-D-maltopyranoside.

7. The method of claim 1, wherein the alkylglycoside is n-hexyl-β-D-glucopyranoside.

8. The method of claim 1, comprising the further step of lyophilizing said second aqueous solution.

9. A method of preventing oxidation of an antibody present in a first aqueous solution, said method comprising the step of adding to said first aqueous solution an oxidation preventing amount of an alkylglycoside having a CMC value of about 1.0 mM or greater in water at 25° C., wherein the alkylglycoside is added to a final concentration that is lower than the CMC value of the alkylglycoside in water at 25° C., thereby providing a second aqueous solution.

10. The method of claim 9, wherein the antibody is a monoclonal antibody.

11. The method of claim 9, wherein the alkylglycoside is selected from the group consisting of n-hexyl-β-D-glucopyranoside, n-heptyl-β-D-glucopyranoside, n-octyl-β-D-glucopyranoside, n-nonyl-β-D-glucopyranoside, n-decyl-β-D-glucopyranoside, 3-cyclohexyl-1-propyl-β-D-glucoside, 3-cyclohexyl-1-butyl-β-D-glucoside, n-hexyl-β-D-maltopyranoside, n-octyl-β-D-maltopyranoside, n-nonyl-β-D-maltopyranoside, n-decyl-β-D-maltopyranoside, cyclohexyl-methyl-β-D-maltoside, 2-cyclohexyl-ethyl-β-D-maltoside, 3-cyclohexyl-propyl-β-D-maltoside, 4-cyclohexyl-butyl-β-D-maltoside, and 5-cyclohexyl-pentyl-β-D-maltoside.

12. The method of claim 9, wherein the alkylglycoside is n-octyl-β-D-glucopyranoside.

13. The method of claim 9, wherein the alkylglycoside is n-decyl-β-D-glucopyranoside.

14. The method of claim 9, wherein the alkylglycoside is n-decyl-β-D-maltopyranoside.

15. The method of claim 9, wherein the alkylglycoside is n-hexyl-β-D-glucopyranoside.

16. The method of claim 9, comprising the further step of lyophilizing said second aqueous solution.

17. The method of claim 9, wherein said oxidation is light-induced oxidation.

18. The method of claim 17, wherein said light-induced oxidation is of tryptophan residues in said antibody.

* * * * *